United States Patent [19]

Hildwein et al.

[11] Patent Number: 5,490,843
[45] Date of Patent: Feb. 13, 1996

[54] FLEXIBLE ENDOSCOPIC SURGICAL PORT

[75] Inventors: Roger L. Hildwein; Robert C. Uschold, both of Cincinnati; J. D. Staley, Jr., Loveland; Paul Riestenberg, Cincinnati; Laura Gallagher, Maineville; Rex Nagao, Cincinnati, all of Ohio

[73] Assignee: Ethicon, Inc., Somerville, N.J.

[21] Appl. No.: 178,200

[22] Filed: Jan. 6, 1994

Related U.S. Application Data

[62] Division of Ser. No. 906,774, Jun. 30, 1992, abandoned.

[51] Int. Cl.$^6$ ............................................. A61B 17/34
[52] U.S. Cl. ................... 604/164; 604/264; 604/272; 606/185
[58] Field of Search ................... 606/185; 604/164, 604/264, 272

[56] References Cited

U.S. PATENT DOCUMENTS

| | | | |
|---|---|---|---|
| 4,423,740 | 1/1984 | Castle et al. | 128/748 |
| 4,452,244 | 6/1984 | Chin | 128/321 |
| 4,535,773 | 8/1985 | Yoon | 604/51 |
| 4,545,374 | 10/1985 | Jacobson | 128/303 R |
| 4,601,710 | 7/1986 | Moll | 604/165 |
| 4,631,051 | 12/1986 | Harris | 604/9 |
| 4,645,492 | 2/1987 | Weeks | 604/174 |
| 4,654,030 | 3/1987 | Moll et al. | 604/165 |
| 4,655,752 | 4/1987 | Honkanen et al. | 604/256 |
| 4,678,463 | 7/1987 | Millar | 604/285 |
| 4,874,378 | 10/1989 | Hillstead | 604/167 |
| 4,931,042 | 6/1990 | Holmes et al. | 604/164 |
| 4,950,257 | 8/1990 | Hibbs et al. | 604/265 |
| 4,978,334 | 12/1990 | Toye et al. | 604/51 |
| 5,009,643 | 4/1991 | Reich et al. | 606/185 X |
| 5,030,206 | 7/1991 | Lander | 604/164 |
| 5,066,288 | 11/1991 | Deniega et al. | 604/274 |
| 5,078,689 | 1/1992 | Keller | 604/167 |
| 5,169,387 | 12/1992 | Kronner | 604/164 X |
| 5,176,648 | 1/1993 | Holmes et al. | 604/164 |
| 5,176,649 | 1/1993 | Wakabayashi | 604/164 |
| 5,226,426 | 7/1993 | Yoon | 128/753 |

FOREIGN PATENT DOCUMENTS

| | | | |
|---|---|---|---|
| 743519 | 4/1933 | France . | |
| 3017065 | 11/1981 | Germany | A61M 27/00 |
| 3507086 | 11/1990 | Germany | A61D 7/00 |
| 1618397A | 1/1991 | U.S.S.R. . | |

*Primary Examiner*—Michael H. Thaler
*Attorney, Agent, or Firm*—Paul A. Coletti

[57] ABSTRACT

A flexible endoscopic surgical port comprises a trocar tube or cannula made partially or entirely of flexible material which can be inserted into a body wall at an intercostal location to allow the insertion and manipulation of endoscopic surgical instruments within the thoracic cavity. The surgical port includes a hollow tubular body which is inserted through an intercostal opening in the body wall extending into the thoracic cavity with an annular flange at one end of the tubular body projecting radially outward and engaging the body wall adjacent to the opening. The flange is able to flex relative to the tubular body whereby the surgical instrument inserted in the tubular body can be manipulated over a wide range of motion inside the thoracic cavity. A retainer ring can be installed at the end of the tubular body opposite to the flange to secure the surgical port in the body wall. Improved obturators are provided for installation of the flexible surgical port.

2 Claims, 18 Drawing Sheets

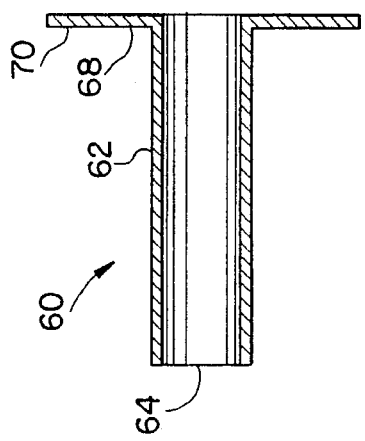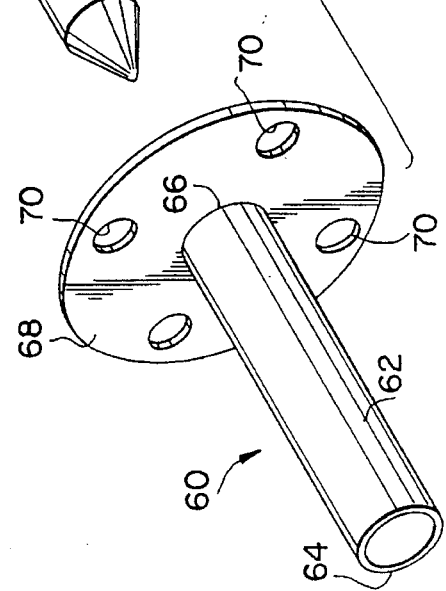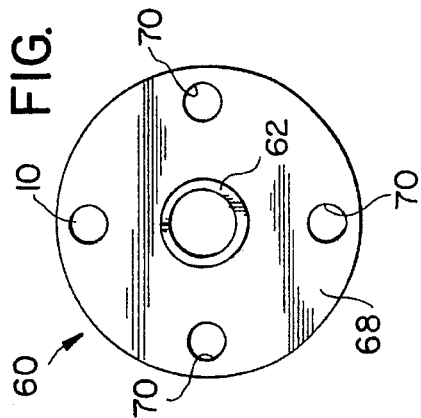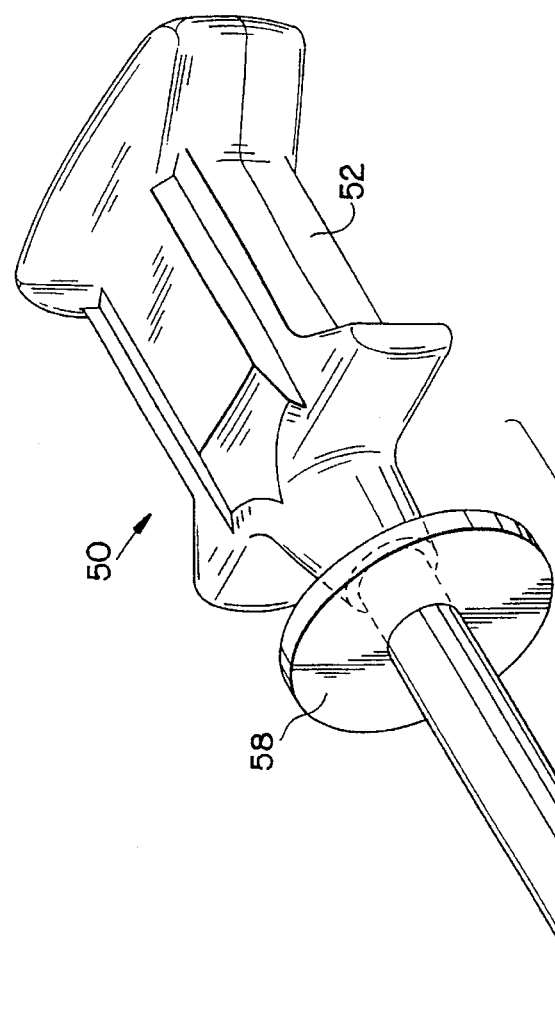

FIG. 4
FIG. 5
FIG. 6
FIG. 7
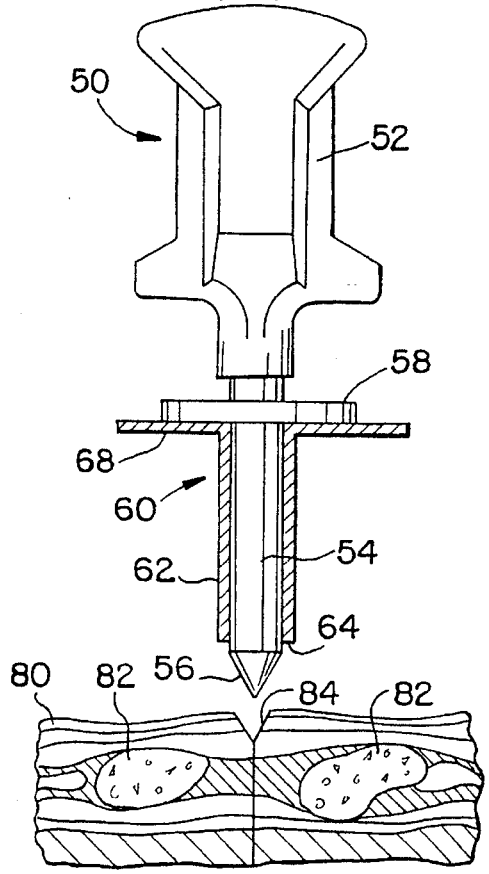
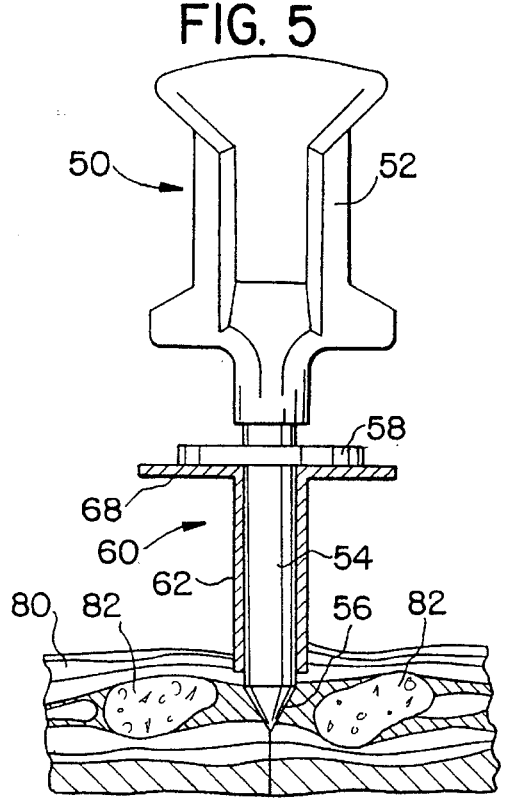
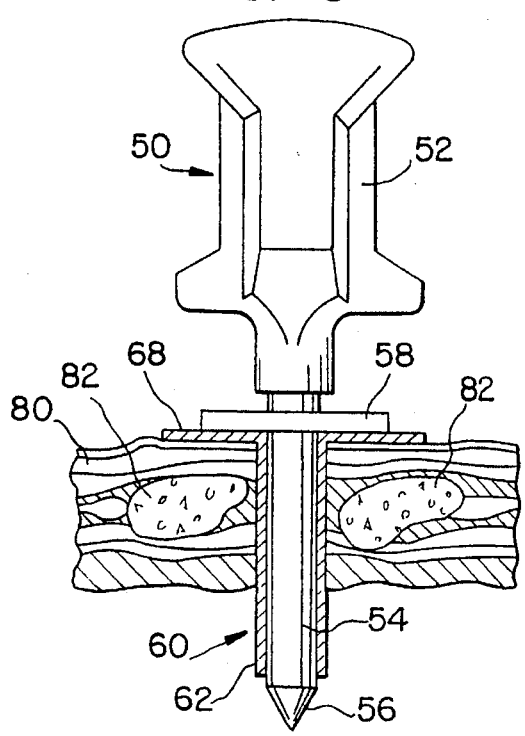
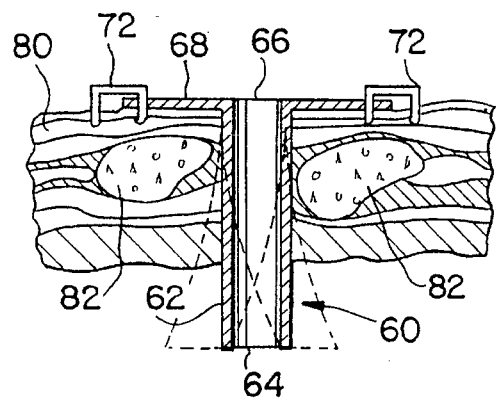

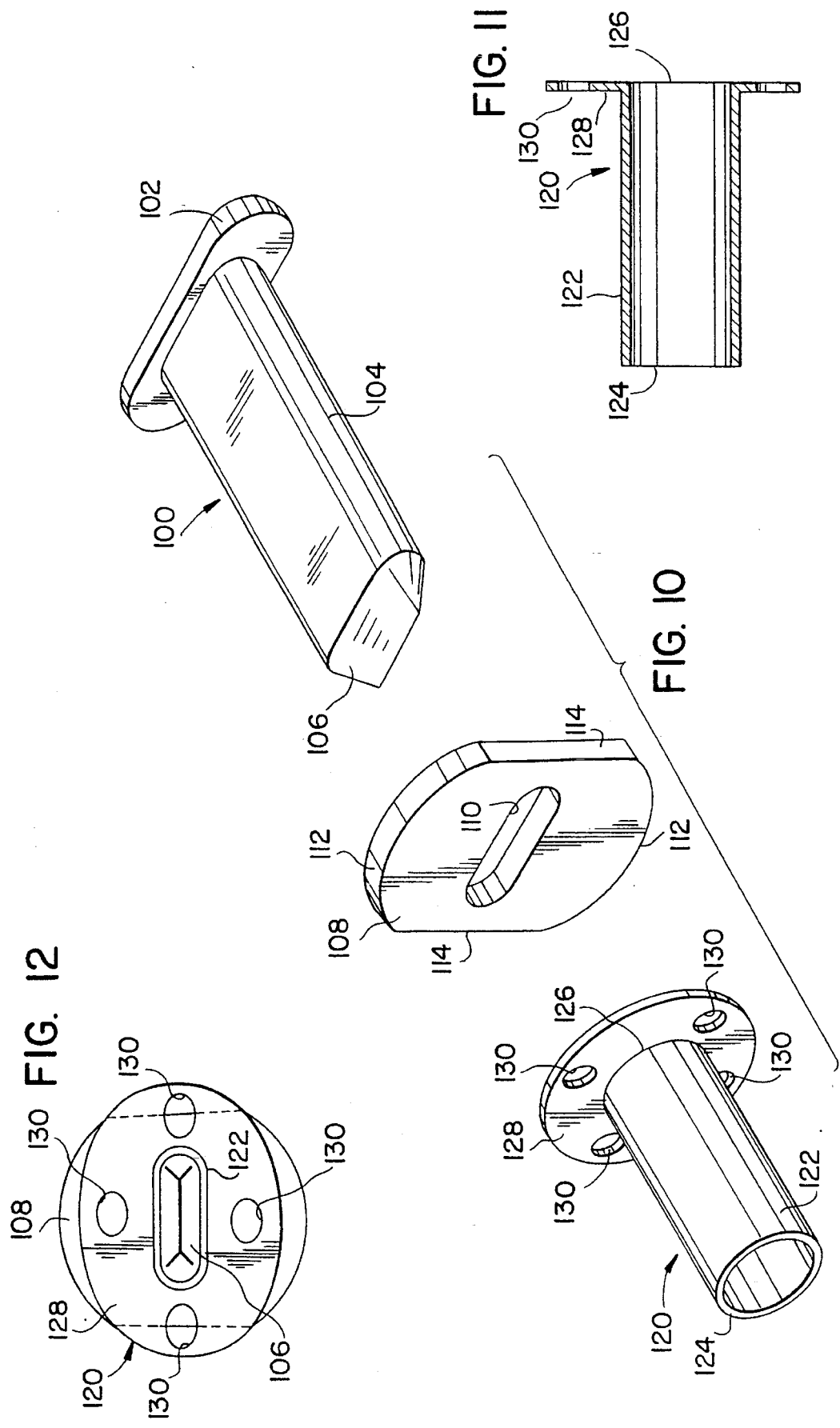

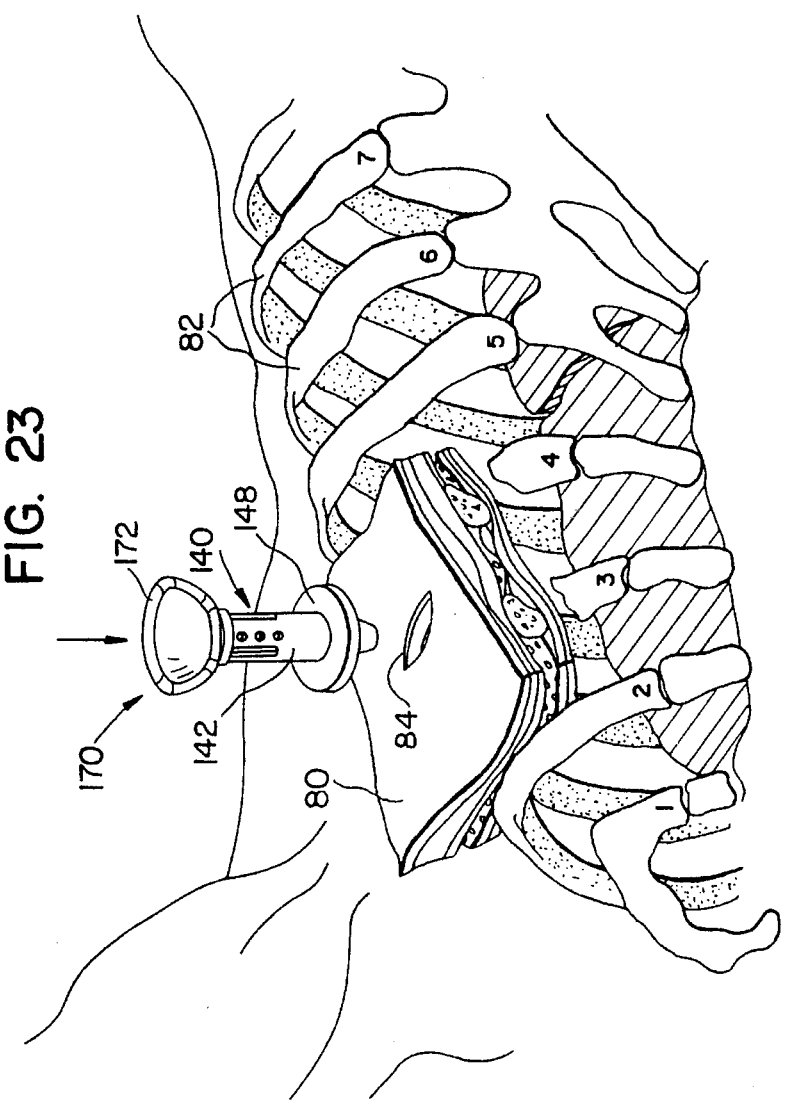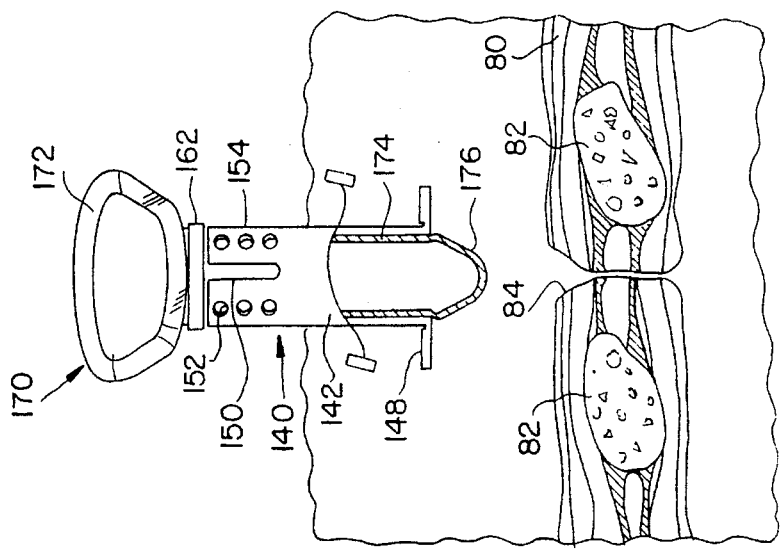

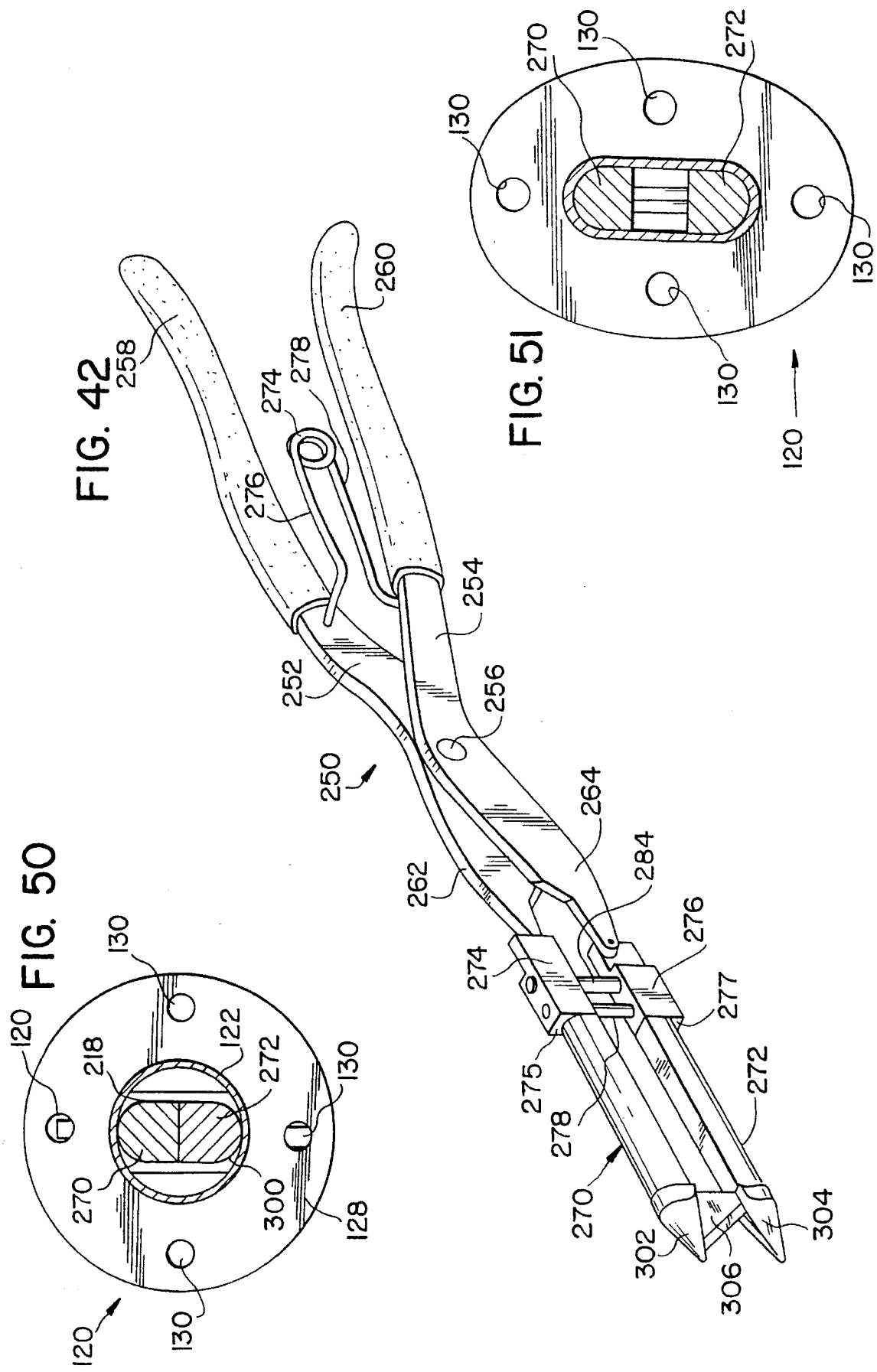

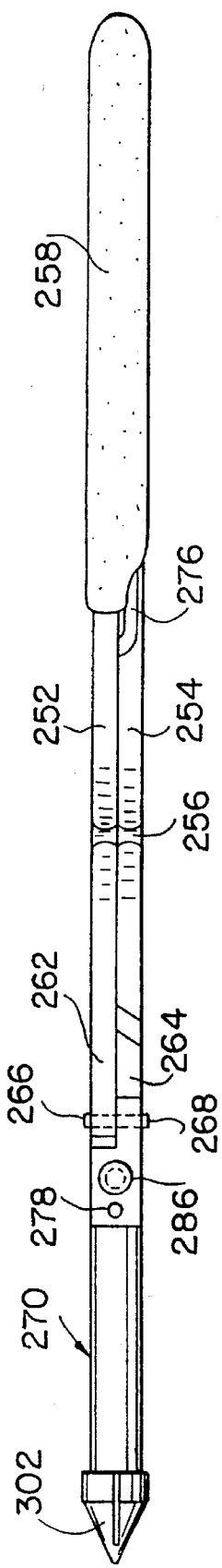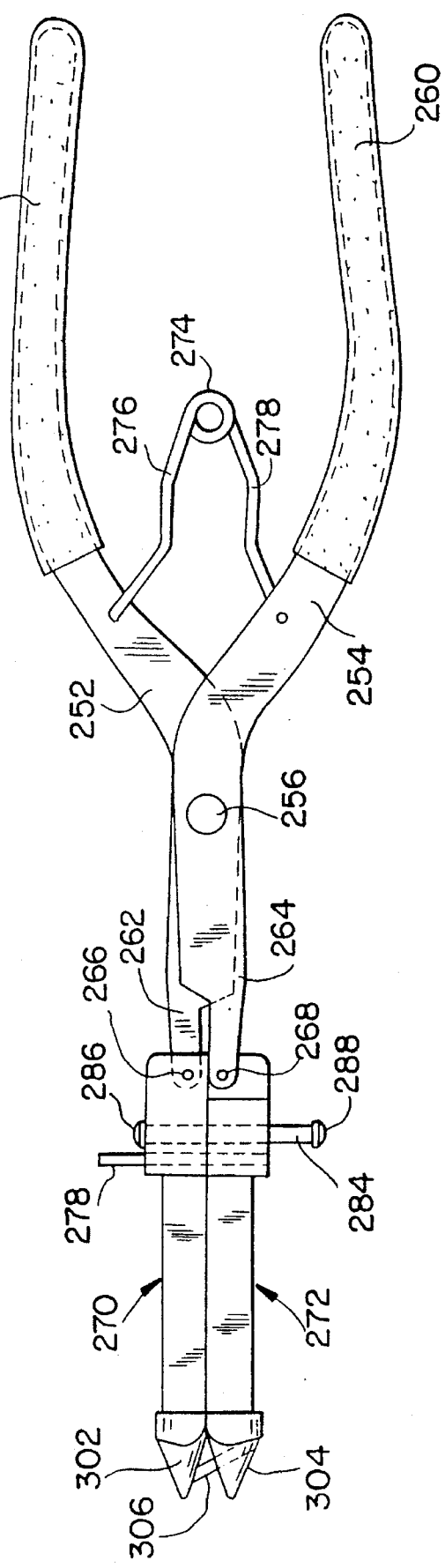

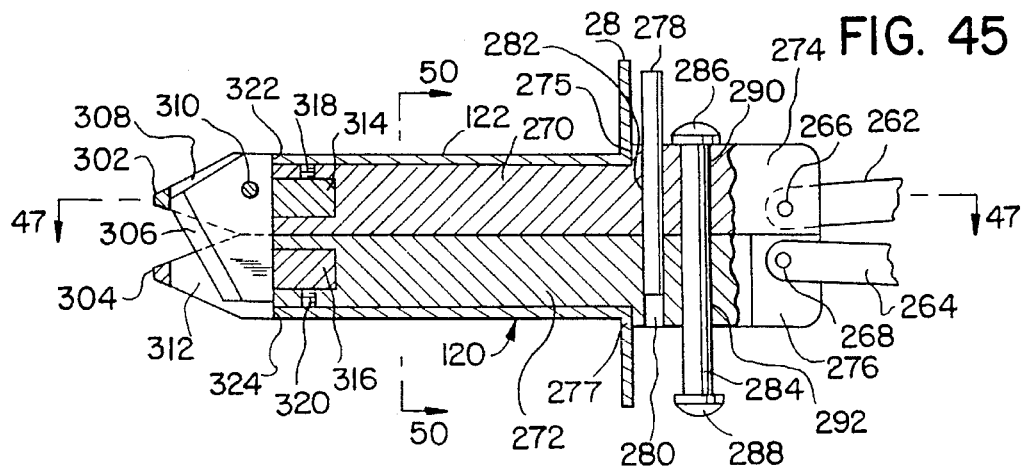
FIG. 45
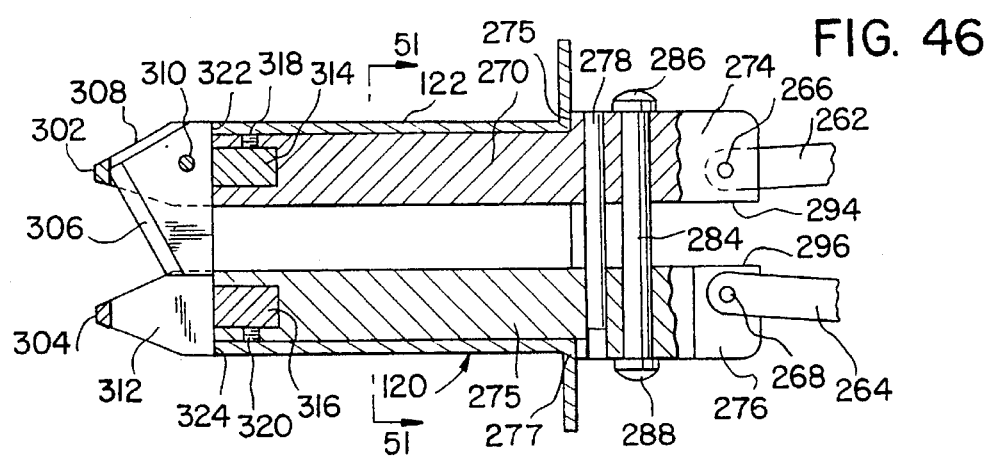
FIG. 46
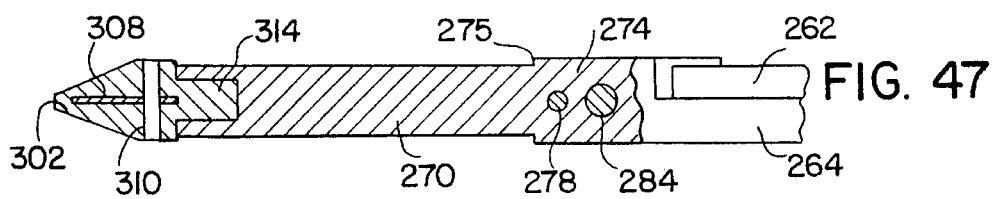
FIG. 47
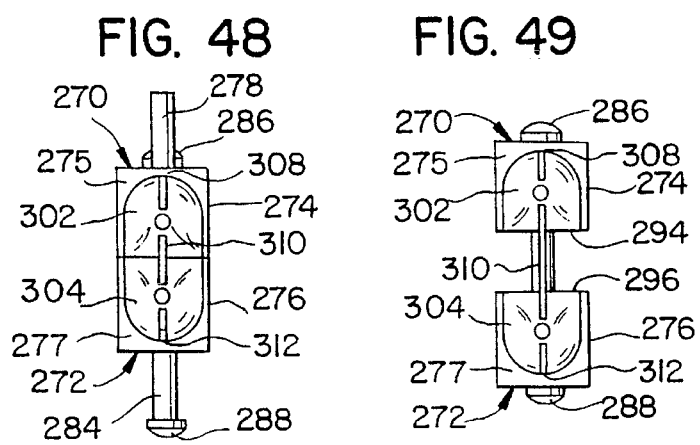
FIG. 48
FIG. 49

FLEXIBLE ENDOSCOPIC SURGICAL PORT

This is a division, of application Ser. No. 07/906,774, filed Jun. 30, 1992, which is hereby incorporated by reference.

FIELD OF THE INVENTION

The present invention generally relates to a flexible endoscopic surgical port and, more particularly, to a trocar tube or cannula made partially or entirely of flexible material which can be inserted into a body wall at an intercostal location to provide a flexible surgical port for the insertion and manipulation of endoscopic surgical instruments within the thoracic cavity. The invention also relates an improved technique of performing surgery through a flexible surgical port extending into the thoracic cavity and to an improved obturator for installing a flexible trocar tube or cannula which provides the surgical port.

BACKGROUND OF THE INVENTION

In the past, endoscopic surgery has been facilitated by the use of trocars as operative surgical ports to gain entrance into the body for insertion and manipulation of surgical instruments. Typically, these trocars or ports have employed a thin, rigid cannula as the passageway for various endoscopic instruments. Often, internal pressures in the body cavity are generated by an external positive pressure source and pressure is introduced internally into the body cavity through the trocar tube or cannula, which often employs valves or gaskets to maintain the internal pressure. An exception to this procedure is thoracoscopy, where internal pressures do not need to be maintained.

Since the maintenance of internal pressures is not required for thoracoscopy, the associated valves and gaskets may be omitted from the trocars used in thoracic procedures. While it is possible for the thoracic surgery to be performed through small incisions, using existing, non-endoscopic instruments, skin sterility is difficult to maintain and damage to the instruments and to the tissue may occur due to abrasion and friction. Thus, it appears that for thoracic surgery, a need exists for using a trocar tube or port to protect the surgical instruments and the body tissue against damage when the instruments are inserted and manipulated inside the body cavity.

Also, since the trocar tube or cannula must be inserted between the ribs for thoracic surgery, a concern about pain arises. A large, rigid trocar tube placed snugly within a relatively small intercostal space may have a tendency to exert pressure upon the intercostal nerve. Also, there is a tendency to disrupt the intercostal nerve by leaning on the instruments. The rigid trocar tube may, as well, limit the motion of the instruments being used to perform the surgery. Thus, it is desirable to provide a trocar tube or cannula for use as a surgical port in thoracoscopy which avoids the concentration of forces at the intercostal location and instead spreads out the forces when the instruments are inserted and manipulated in the body cavity. Also, it is desirable to provide a surgical port which allows a wide range of motion and use of curved instruments or instruments with non-round cross sections.

SUMMARY OF THE INVENTION

The present invention recognizes that a soft or malleable trocar tube can be used to avoid pain and to protect the tissue and surgical instruments in performing thoracic surgery. While flexible trocars are known in the prior art, none has been provided with a variable cross section which is conformable to the available intercostal spacing of individual patients. The present invention achieves this objective and provides a trocar tube Which permits a wide range of motion for the manipulation of endoscopic surgical instruments in the thoracic cavity. The invention also provides an obturator to facilitate the insertion of the trocar tube or cannula into an intercostal space.

The present invention provides an improved surgical port which comprises a totally flexible grommet-like structure. The surgical port generally comprises a hollow, thin-walled flexible tubular body provided with a thin-walled flexible annular flange at one end of the tubular body. Both the tubular body and the flange consist of flexible, resilient material, e.g., elastomeric material. Preferably, the tubular body and the flange of the flexible port have a circular cross section, although other alternative configurations, such as ovoid, can be employed if desired. For example, the internal diameter of the tubular body or cannula is normally in the range of 5 to 20 mm., or more, although other sizes such as larger oval shapes may be employed, if desired.

When the surgical port is inserted into an intercostal opening in the body wall for thoracic surgery, the flange may be placed either internally or externally relative to the body wall. When placed externally, the flange can be attached to the body wall by staples, sutures, adhesives, or any other suitable means to the body wall. With the flange placed internally, the outer unflanged end of the surgical port is divided longitudinally into a plurality of flaps which are bent downward and secured to the external surface of the body wall by staples, sutures, adhesives or other suitable fasteners. Alternatively, with the flange placed internally, the flaps at the outer end of the port can be secured to a retainer ring.

An obturator is commonly used to insert the trocar tube into an intercostal space through an opening cut in the body wall. If the diameter of the trocar tube is too large to fit within the intercostal space, the trocar tube may be stretched into an oval shaped cross section by using either an oval shaped obturator or an obturator of variable geometry, or the outside diameter may be compressed for insertion of the trocar tube. When the obturator is removed, the trocar tube is pinched between the ribs so that the cross section of the trocar tube varies from its proximal end to its distal end. Alternatively, if the diameter of the trocar tube is small enough to fit between the ribs without being stretched into an oval shape, a circular shaped obturator can be used to insert the trocar tube in the intercostal space.

The trocar tube or cannula can be installed at an intercostal space in the body wall with its flange external to the thoracic cavity. The end of the trocar tube distal to the flange may be inserted into an opening in the body wall by use of the obturator until the flange is positioned in contact with the external surface of the body wall. Then the obturator is pulled out of the trocar tube while retaining the trocar tube in place within the body wall. When an obturator of variable geometry is used, the obturator shape or cross section is contracted prior to pulling the obturator out of the trocar tube. After the flange is secured in place on the body wall, surgical instruments may be inserted through the trocar tube and manipulated inside the body cavity to perform the desired surgical procedures.

Alternatively, the trocar tube or cannula can be installed at an intercostal space on the body wall with its flange internal to the thoracic cavity. The trocar tube is inserted through the opening in the body wall with the flange positioned at the distal end of the trocar tube inside the body cavity. After the trocar tube is inserted in this fashion, the flange is spread out into contact with the internal surface of the body wall. With the flange contacting the internal surface of the body wall, the trocar tube presents an extremely clean internal profile which allows the maximum visualization and range of motion of the surgical instruments. Additionally, the proximal end of the trocar tube at the external surface of the body wall may be cut longitudinally into a plurality of flaps which are bent downward and secured to the external body surface by staples, sutures or other suitable fasteners. The trocar tube is adjustable to variable thicknesses of the body wall by varying the length of the cuts made at the external end of the trocar tube. Also, the cut sections or flaps of the trocar tube can be tensioned as desired.

In a preferred embodiment of the surgical port, a retainer ring is placed on the external surface of the body wall surrounding the external or proximal portion of the trocar tube. Suitable fastener means is provided for attaching the ring to the cut sections or flaps of the trocar tube which are bent downward into engagement with the ring. The fastener means may be embodied as hook-like protrusions on the ring which are received in partially formed holes or weakened areas provided on the cut sections or flaps of the trocar tube. A plurality of longitudinally spaced partially formed holes or weakened areas can be formed in the trocar tube to provide an adjustable retention feature.

In another embodiment, the surgical port comprises a pair of spaced parallel stay rods with a flexible band connecting the mid-sections of the stay rods together. The stay rods are adapted for insertion through an intercostal opening in the body wall extending into the thoracic cavity with the flexible band located within the opening. Each of the stay rods is adapted to bend outwardly at its proximal and distal ends into engagement with the body wall to protect the body wall from trauma when a surgical instrument is inserted and manipulated in the surgical port. The stay rods may consist of malleable material which can be bent manually after insertion of the surgical port into the intercostal opening. Alternatively, the stay rods may consist of memory alloy which is temperature activated, e.g., by body heat, after insertion of the surgical port into the intercostal opening to bend the stay rods into the desired configuration.

Another aspect of the invention relates to an obturator of variable geometry for inserting a flexible trocar tube into an opening at an intercostal location in a body wall. The obturator comprises a pair of elongated jaw members mounted for movement laterally toward and away from each other. The obturator includes means for moving the jaw members laterally relative to each other from a closed position to an open position to vary the separation between the jaw members. The jaw members when closed are adapted to be inserted into the flexible trocar tube and the jaw members when opened are adapted to stretch the flexible trocar tube into an ovoid shape which is sufficiently narrow in width to fit between the ribs in the body wall at the intercostal location. The obturator is provided with knife means located between the jaw members for cutting the tissue at the intercostal location as the jaw members are inserted in the body wall. Also, the obturator includes means for maintaining the jaw members in parallel alignment as the jaw members are moved laterally relative to each other. Further, the obturator is provided with means for limiting the maximum separation of the jaw members.

The invention is also embodied in a trocar assembly comprising an elongated trocar obturator with a collar spaced proximally from the distal end of the obturator and an elongated trocar tube of flexible material comprising a hollow tubular body with an annular flange projecting radially outward from one end of the tubular body. The trocar obturator is insertable into the hollow tubular body of the trocar tube with the collar on the obturator engaging the flange on the trocar tube and the distal end of the obturator extending from the hollow tubular body for inserting the trocar tube into an opening at an intercostal location in a body wall. The collar may be slidably mounted on the trocar obturator and adapted to remain in engagement with the flange as the trocar obturator is withdrawn from the trocar tube. Also, the obturator may have an oval-shaped cross section adapted to stretch the flexible trocar tube into an ovoid shape sufficiently narrow in width to fit between the ribs at the intercostal location in the body wall.

BRIEF DESCRIPTION OF THE DRAWINGS

The foregoing and other objects, aspects and advantages will be better understood from the following detailed description of the preferred embodiments of the invention with reference to the drawings, in which:

FIG. 1 is a perspective view of a trocar for installing a trocar tube or cannula constructed in accordance with the invention;

FIG. 2 is a longitudinal section of the trocar tube or cannula of FIG. 1;

FIG. 3 is a distal end view of the trocar tube or cannula;

FIGS. 4–7 illustrate the installation of the trocar tube or cannula of FIG. 1;

FIG. 10 is a perspective view of another trocar for installing a trocar tube or cannula of a relatively large diameter constructed in accordance with the invention;

FIG. 11 is a longitudinal section of the trocar tube or cannula of FIG. 10;

FIG. 12 is a distal end view of the trocar tube or cannula with the trocar inserted therein prior to installation;

FIGS. 23–31 illustrate the procedure for installing the trocar tube or cannula of FIGS. 20–22 in a body wall;

FIG. 39 shows the trocar tube or cannula of

FIG. 38 installed in a body wall;

FIG. 41 shows the trocar tube or cannula of

FIG. 40 installed in a body wall;

FIG. 42 is a perspective view of an obturator with jaws of variable geometry for installing a trocar tube or cannula of relatively large diameter;

FIG. 43 is a side elevation view of the obturator of FIG. 42;

FIG. 44 is a top view of the obturator of FIG. 42;

FIG. 45 is an enlarged, partially cutaway side view showing the obturator jaws closed and inserted in the trocar tube or cannula;

FIG. 46 is an enlarged, partially cutaway side view showing the obturator jaws open to flex the trocar tube or cannula into an ovoid shape;

FIG. 47 is an enlarged, horizontal section of one of the obturator jaws taken along line 47—47 of FIG. 45;

FIG. 48 is a front or distal end view of the obturator jaws in the closed position;

FIG. 49 is a front or distal end view of the obturator jaws in the closed position;

FIG. 50 is a vertical section of the closed obturator jaws and the trocar tube or cannula taken along line 50—50 of FIG. 45; and FIG. 51 is a vertical section of the open obturator jaws and the trocar tube or cannula taken along line 51—51 of FIG. 46.

DETAILED DESCRIPTION OF PREFERRED EMBODIMENTS

Figure 8:
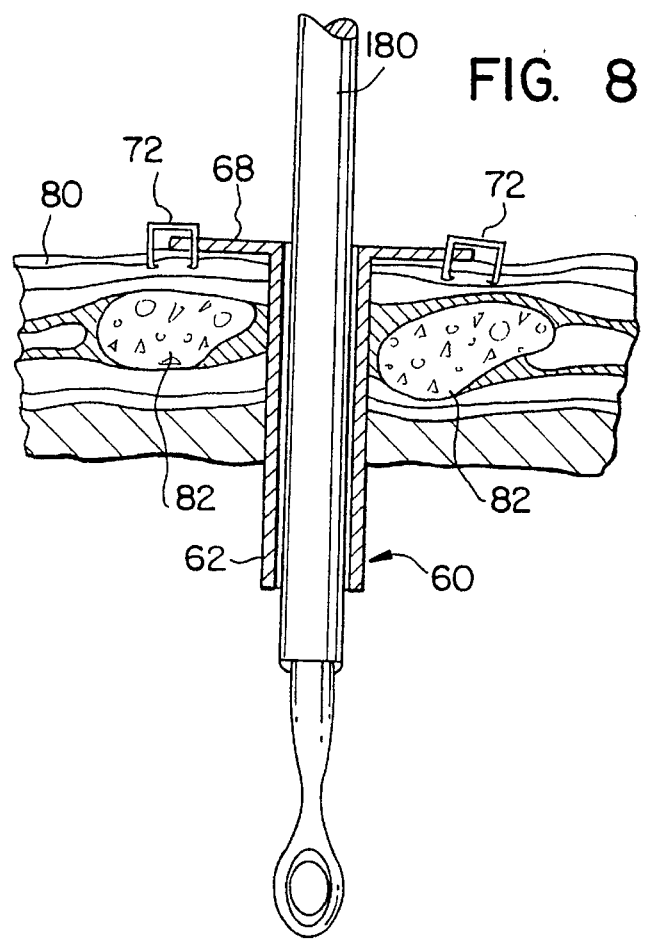
FIG. 8 illustrates the insertion of an endoscopic surgical instrument into the trocar tube or cannula of FIG. 1.

Referring to FIG. 1, a trocar, generally 50, is shown which is adapted to install a trocar tube or cannula, generally 60, through a body wall to provide a surgical port which allows surgical instruments to be inserted and manipulated inside a body cavity. The trocar 50 includes a trocar handle 52 which supports an elongated, cylindrical obturator 54 provided with a conically tapered, pointed distal end 56. A circular flange or collar 58 is mounted at a fixed proximal position on the obturator 54 adjacent to the trocar handle 52.

The trocar tube or cannula 60 comprises an elongated hollow tubular body 62 having an open distal end 64 and an open proximal end 66 provided with a flat, annular flange 68 extending radially outward from the tubular body 62. A plurality of circumferentially spaced holes 70 is provided in the annular flange 68, if desired, to facilitate the attachment of the flange 68 to the surface of the body wall. The trocar tube or cannula 60 consists of a thin-walled construction made of elastomeric material which is flexible and resilient. The material and wall thickness of the trocar tube or cannula 60 are selected such that the flange 68 is sufficiently flexible to bend or flex in any direction relative to the tubular body 62 without appreciable distortion of the tubular body 62. Also, the wall thickness and material of the trocar tube or cannula 60 are selected such that the tubular body 62 can be readily flexed into an oval-shaped cross section, if necessary, to fit between the adjacent ribs at an intercostal space in the body wall.

The trocar tube or cannula 60, shown in FIGS. 1–3, has a relatively small inner diameter, e.g., 10 mm., which is small enough to fit between the adjacent ribs in an intercostal space of the body wall without any appreciable distortion from its circular shape. The trocar tube or cannula 60 is made of an elastomeric material, e.g., polyeurathane. The wall thickness of the tubular body 62 and the flange 68 is approximately 1.0 mm. Four holes 70 are circumferentially spaced about the periphery of the flange 68 at equal angular intervals, e.g., approximately 90 degrees apart, for receiving staples, sutures or other fasteners to secure the flange 68 to the external surface of the body wall.

Referring to FIGS. 4–7, the procedure is shown for installing the trocar tube or cannula 60 into a body wall 80 at an intercostal space between a pair of adjacent ribs 82. The trocar 50 is inserted into the trocar tube or cannula 60 with the trocar flange 58 engaging the annular flange 68 of the trocar tube 60. The obturator 54 extends through the tubular body 62 with the pointed end 56 extending beyond the distal end 64 of the tubular body 62. A slit or opening 84 (FIG. 4) is cut into the body wall 80 at the desired intercostal location. The trocar 50 is manually moved to align the pointed end 56 of the obturator 54 with the intercostal opening 84. Then the trocar 50 is pushed downward to insert the obturator 54 and the trocar tube or cannula 60 into the body wall 80. The trocar flange 58 engages the annular flange 68 on the trocar tube or cannula 60 and advances the tubular body 62 into the body wall 80 as the trocar 50 is pushed downward (FIG. 5).

The trocar tube or cannula 60 is pushed downward by the trocar 50 until the annular flange 68 engages the external surface of the body wall 80 (FIG. 6). Then the trocar 50 is pulled upwardly to remove the obturator 54 from the trocar tube or cannula 60. Thereafter, if desired, the annular flange 68 is secured to the external surface of the body wall 80 by one or more surgical staples 72 (FIG. 7) which extend through the holes 70 in the flange 68. Alternatively, the flange 68 can be secured to the body wall 80 by sutures, adhesives, or other suitable fasteners.

Figure 9:
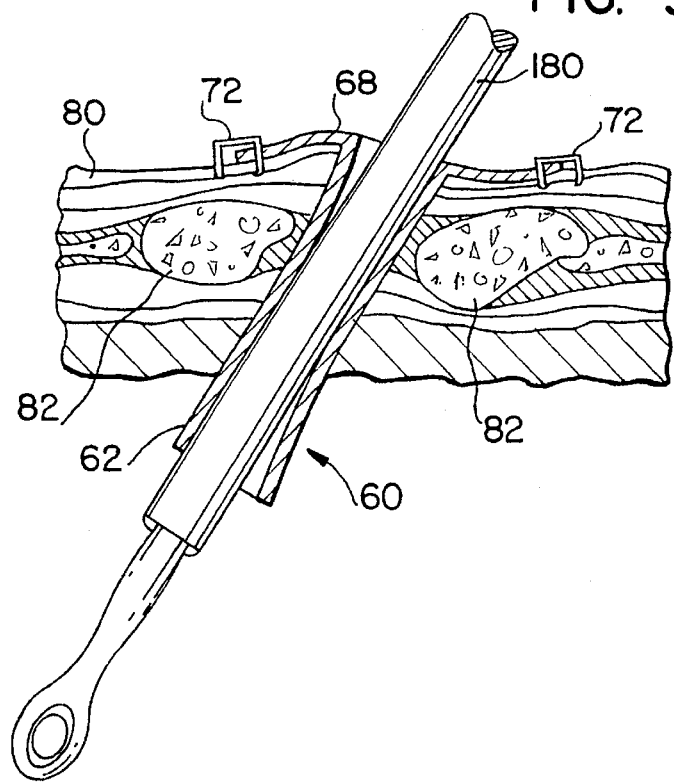
FIG. 9 illustrates the flexing of the trocar tube or cannula of FIG. 1 when the instrument is manipulated from side to side.
Figure 13:
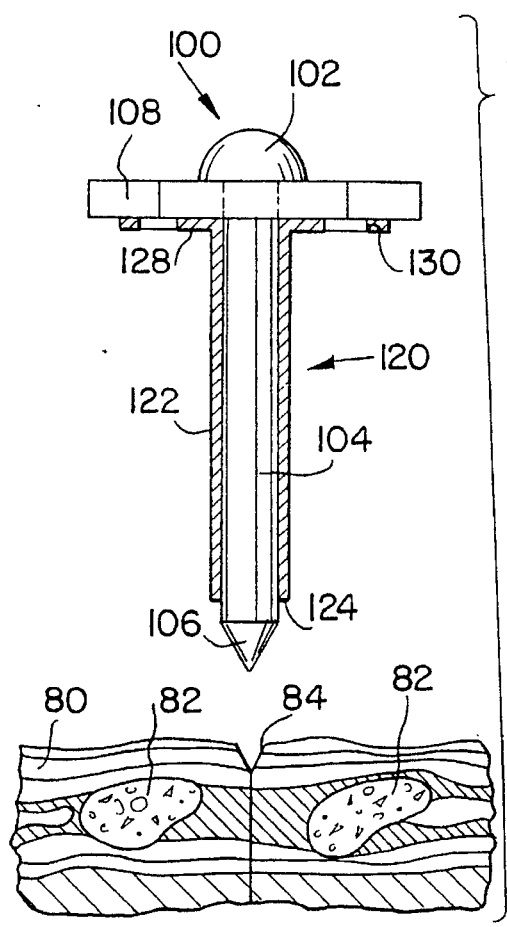
FIGS. 13–16 illustrate the installation of the trocar tube or cannula of FIG. 10.

As shown in FIGS. 8 and 9, the trocar tube or cannula 60 provides a flexible surgical port which enables surgical instruments, e.g. a grasping forceps 180, to be inserted and manipulated within the thoracic cavity. The annular flange 68 is sufficiently flexible to allow the tubular body 62 to be flexed from side to side to provide a relatively wide range of angular displacement. For example, when the trocar tube 60 is flexed from side to side transversely relative to the ribs 82, a total angular range of approximately 90 to 110 degrees is available for manipulation of the surgical instruments inside the body cavity. Also, when the trocar tube or cannula 60 is flexed from side to side longitudinally between the adjacent ribs 82, a total angular range of approximately 120 to 150 degrees is available for manipulation of the surgical instruments inside the body cavity.

In the embodiment of FIG. 10, a trocar, generally 100, includes a push head or handle 102 which supports an elongated, oval-shaped obturator 104 having a tapered, pointed tip 106. The trocar 100 includes a slidable flange or collar 108 having an oval-shaped slot 110 extending therethrough for slidably receiving the oval-shaped obturator 104. The slidable flange or collar 108 has rounded edges 112 at the top and bottom and flat edges 114 at its opposite sides.

The oval-shaped obturator 100 is provided for installing a trocar tube or cannula 120 including a tubular body 122 with a relatively large diameter, e.g., 20 mm., compared with the intercostal spacing of the adjacent ribs in the body wall. The tubular body 122 has an open distal end 124 and an open proximal end 126 provided with an annular flange 128 projecting outward radially from the tubular body 122. Four holes 130 are circumferentially spaced about the flange 128 at equal angular intervals for receiving staples, sutures or other suitable fasteners to secure the flange 128 to the external surface of the body wall.

Referring to FIGS. 13–16, the procedure is shown for installing the trocar tube or cannula 120 in the body wall 80 at an intercostal location between the adjacent ribs 82. The trocar 100 with the trocar flange 108 slidably mounted on the obturator 104 is inserted into the trocar tube or cannula 120 with the trocar flange 108 engaging the handle 102 and the annular flange 128 of the trocar tube. 120. The obturator 104 extends through the tubular body 122 with the pointed end 106 extending beyond the distal end 124 of the tubular body 122. As shown in FIG. 12, the tubular body 122 of the trocar tube or cannula 120 is flexed into a ovoid shape by the obturator 104. A slit or opening 84 (FIG. 13) is cut into the body wall 80 at the desired intercostal location. The trocar 100 is manually moved to align the pointed end 106 of the obturator 104 with the intercostal opening 84. Then the trocar 100 is pushed downward to insert the obturator 104 and the trocar tube or cannula 120 into the body wall 80. The trocar flange 108 engages the annular flange 128 on the trocar tube or cannula 120 and advances the tubular body 122 into the body wall 80 as the trocar 100 is pushed downward.

Figure 14:
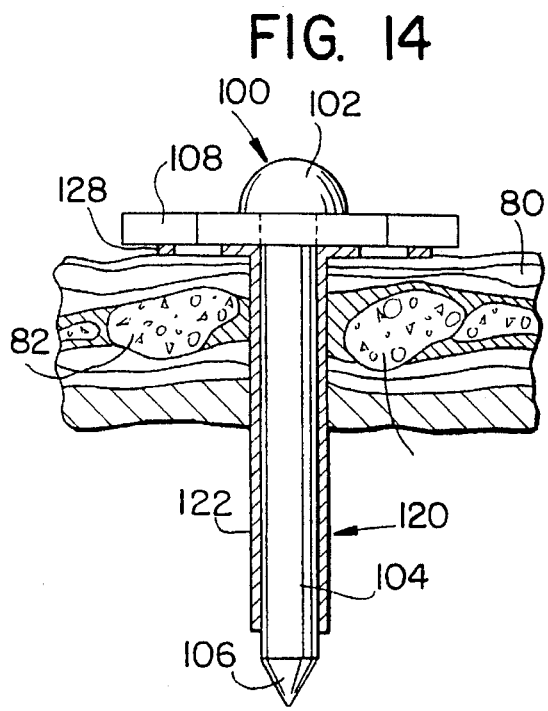
Figure 15:
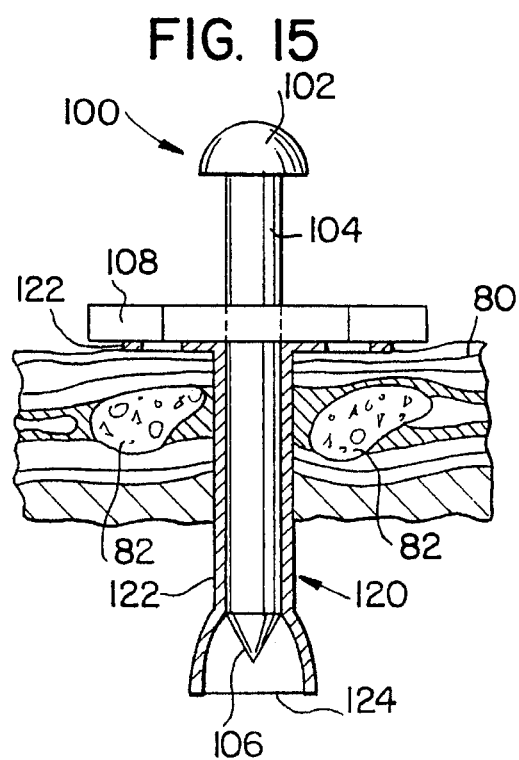

The trocar tube or cannula 120 is pushed downward by the trocar 100 until the annular flange 128 engages the external surface of the body wall 80 (FIG. 14). Then the trocar handle 102 is pulled upwardly to remove the obturator 104 from the trocar tube or cannula 120 which is held in place by pressing downward on the trocar flange 108 to hold the annular flange 128 of the trocar tube 120 against the external surface of the body wall 80 (FIG. 15). As the oval-shaped obturator 104 is withdrawn, the distal end 124 and proximal end 126 of the tubular body 122 tend to return to the natural circular cross section. Thereafter, if desired, the annular flange 128 is secured to the external surface of the body wall 80 by a set of surgical staples 132 (FIG. 16) extending through the holes 130 in the flange 128. Alternatively, the flange 128 can be secured to the body wall 80 by sutures, adhesives or other suitable fasteners.

Figure 16:
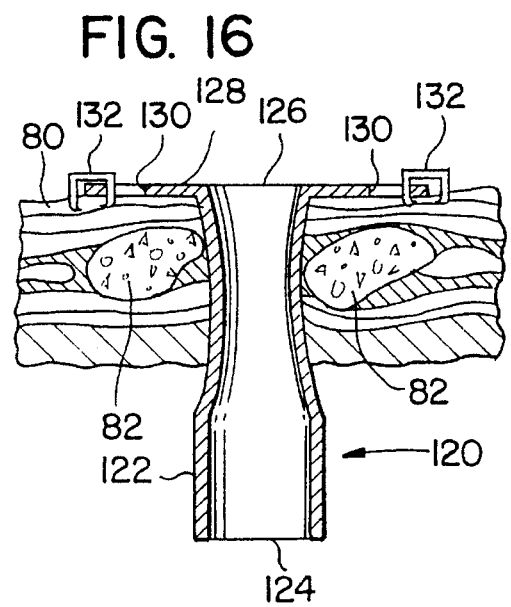
Figure 16A:
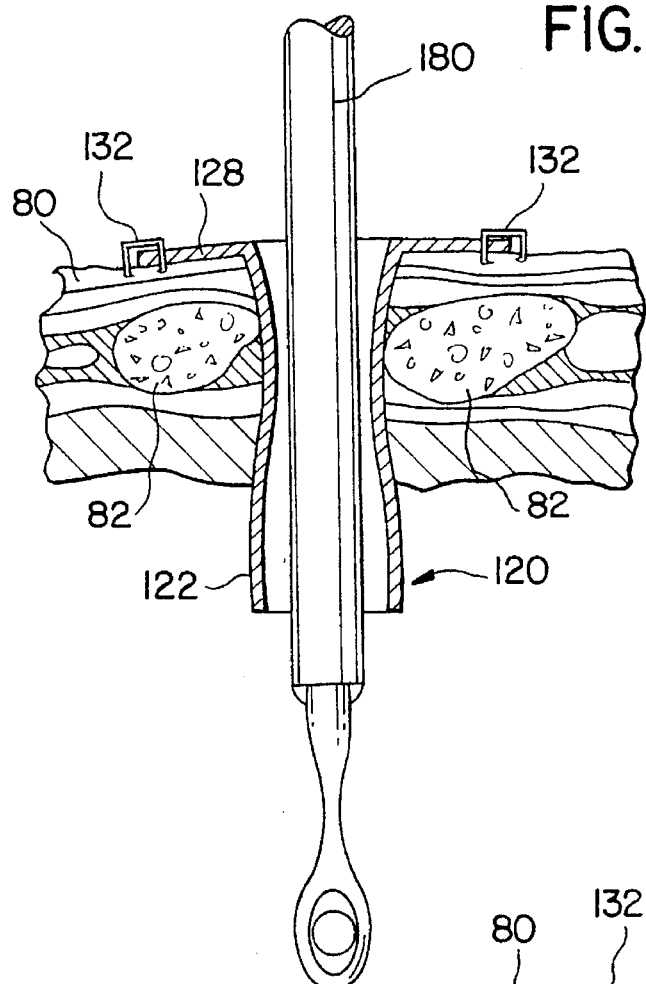
FIG. 16A illustrates the insertion of an endoscopic surgical instrument into the trocar tube or cannula of FIG. 10.
Figure 16B:
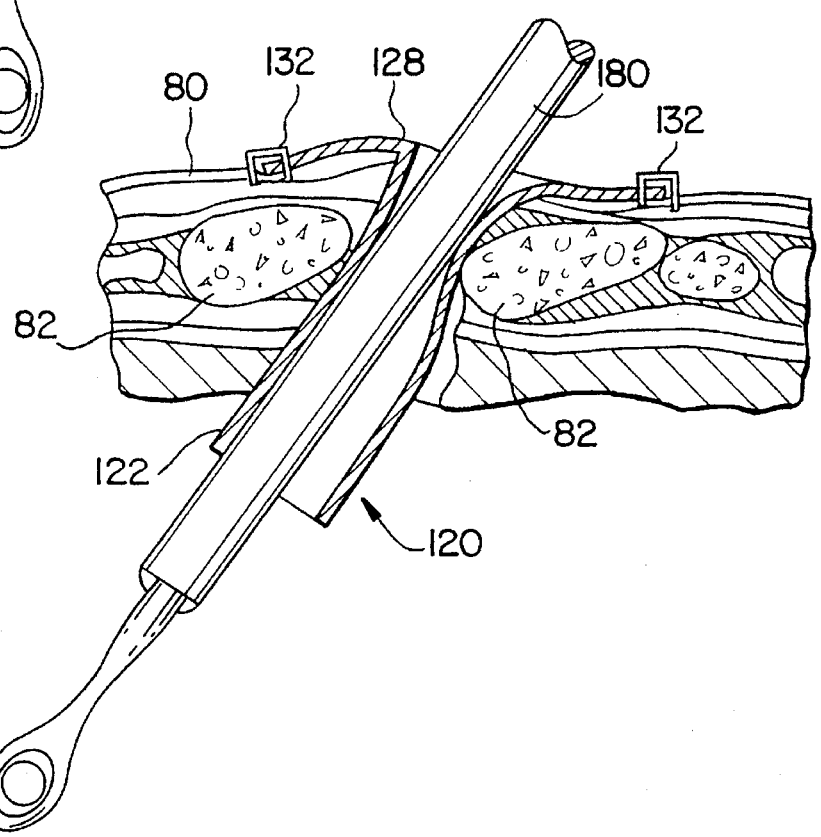
FIG. 16B illustrates the flexing of the trocar tube or cannula of FIG. 10 when the instrument is manipulated from side to side.

As shown in FIGS. 16A and 16B, the trocar tube or cannula 120 provides a flexible surgical port which enables surgical instruments to be inserted and manipulated within the thoracic cavity. The annular flange 128 is sufficiently flexible to allow the tubular body 122 to be flexed from side to side to provide a relatively wide range of angular displacement. For example, when the trocar tube 120 is flexed from side to side transversely relative to the ribs 82, a total angular range of approximately 90 to 110 degrees is available for manipulation of the surgical instruments inside the body cavity. Also, when the trocar tube or cannula 120 is flexed from side to side longitudinally between the adjacent ribs 82, a total angular range of approximately 120 to 150 degrees is available for manipulation of the surgical instruments inside the body cavity.

Figure 17:
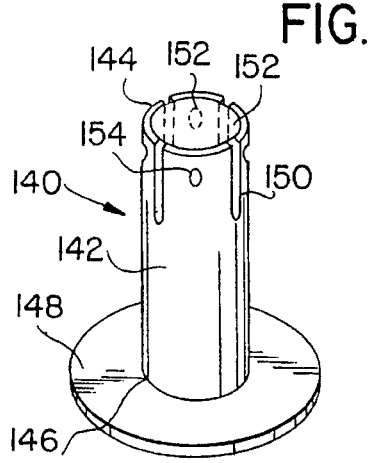
FIGS. 17–19 show another embodiment of the trocar tube or cannula having its outer ends divided into a plurality of flaps to be fastened to the body wall.
Figure 18:
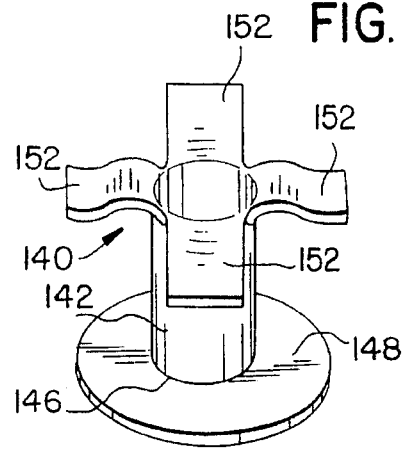
Figure 19:
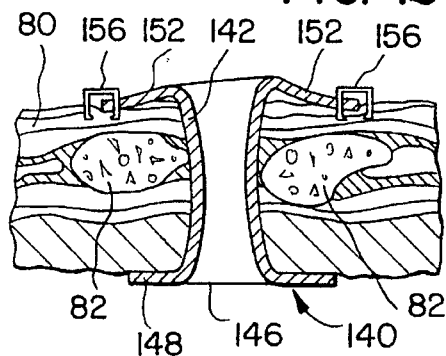

Referring to FIGS. 17–19, a trocar tube or cannula 140 includes a tubular body 142 having an open proximal end 144 and an open distal end 146 provided with an annular flange 148 projecting radially outward from the tubular body 142. The trocar tube or cannula 140 is installed as a surgical port with the annular flange 148 located inside the thoracic cavity in engagement with the internal surface of the body wall 80. The tubular body 142 is longitudinally scored at its outer or proximal end 144 to provide a plurality of thinned strips or score lines 150 which facilitate the separation of the proximal end 144 into a plurality of flaps 152 capable of bending downward into engagement with the external surface of the body wall 80. The trocar tube or cannula 140 is adjustable to variable thicknesses of the body wall 80 by the length of the cuts made along the score lines 150 at the outer or proximal end 144 of the tubular body 142. Each flap 152 is provided with a a partially formed hole 154 comprising a thinned or weakened area, if desired, for receiving a surgical staple 156 to secure the flap 152 to the body wall 80. Alternatively, sutures, adhesives, or other suitable fasteners can be used to secure the flaps 152 to the body wall 80.

Figure 20:
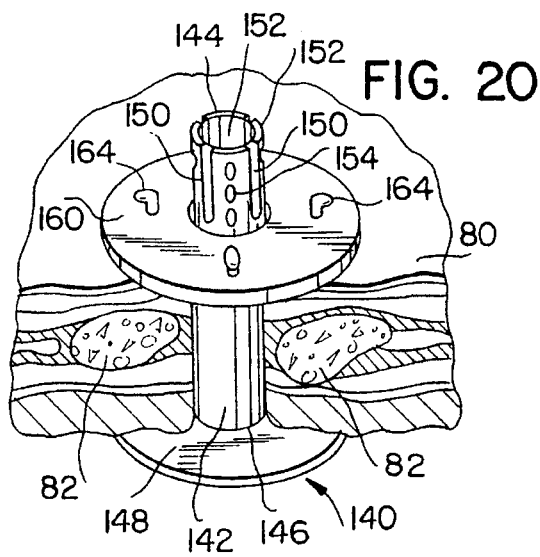
FIGS. 20–22 show another embodiment of the trocar tube or cannula having its outer end divided into a plurality of flaps for attachment to a retainer ring.
Figure 21:
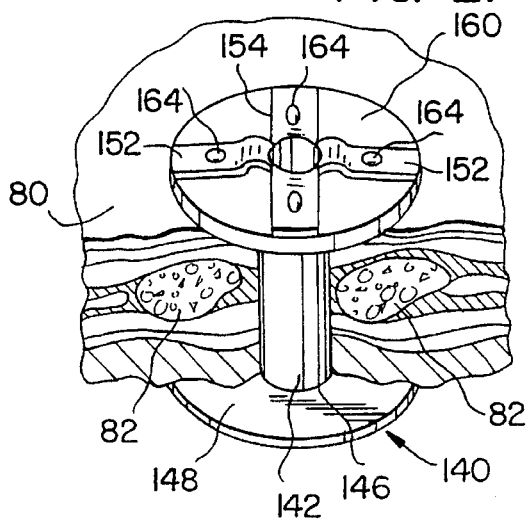
Figure 22:
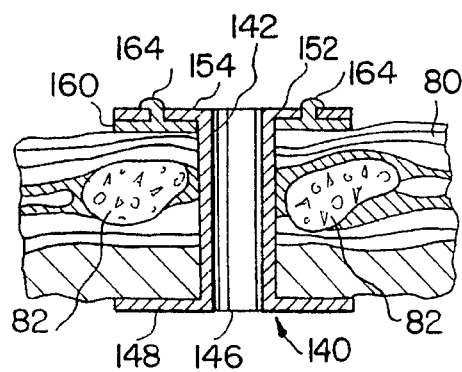

Referring to FIGS. 20–22, in a preferred embodiment of the trocar tube or cannula 140, a flat, annular retainer ring 160 is provided with a central opening 162 which allows the ring 160 to be slipped over the outer or proximal end 144 of the tubular body 142 into engagement with the external surface of the body wall 80. The ring 160 is provided with a plurality of attachment devices, e.g., a series of circumferentially spaced hook-like protrusions 164, for attaching the flaps 152 of the tubular body 142 to the ring 160. The hook-like protrusions 164 are uniformly spaced apart about the circumference of the ring 160 for alignment with the partially formed holes 154 when the flaps 152 are bent downward toward the ring 160. Each flap 152 has one or more partially formed holes or weakened areas 154 arranged in a longitudinal row to permit adjustment of the trocar tube or cannula 140 to accommodate various thicknesses of the body wall 80. The rows of partially formed holes or weakened areas 154 also permit the tension in the flaps 152 to be adjusted.

When the flaps 152 are bent downward into engagement with the retainer ring 160, each hook-like protrusion 164 is punched into one of the partially formed holes or weakened areas 154 to secure the flaps 152 to the retainer ring 160. Alternatively, other attachment devices, such as Velcro™, can be used to secure the flaps 152 to the ring 160. Preferably, the partially formed holes or weakened areas 154 are recessed indentations or thinned areas which are not punched through until the flaps 152 are pressed into engagement with the retainer ring 160.

In the preferred embodiment, the trocar tube or cannula 140 consists of elastomeric material, e.g., polyeurathane, which is flexible and resilient. The ring 160 can be comprised of a stiff rigid material, a soft flexible material, or a combination of both materials in which the soft flexible material is used for an inner portion of the ring 160 adjacent to the tubular body 142 and the stiff rigid material is used for an outer portion of the ring 160. This construction of the ring 160 may be achieved by co-molding techniques.

Referring to FIGS. 23 and 24 the trocar tube or cannula 140 is installed by using a trocar, generally 170, comprising a handle 172 which supports an elongated obturator 174 provided with a pointed distal tip 176 and an annular flange 168 adjacent to the handle 172. The obturator 174 is oval in cross section or has a variable geometry to allow the trocar tube 140 to be received in the intercostal spacing of the adjacent ribs 82 in the body wall 80.

The obturator 170 is inserted into the unflanged end of the trocar tube or cannula 140 so that the flange 148 is located adjacent to the pointed distal end 176 of the obturator 174. An incision 84 is made at intercostal location in the body wall 80 where it is desired to insert the trocar tube or cannula 140. The trocar 170 is manually moved into proximity with the incision 84 and the pointed distal end 176 of the obturator 174 is aligned with the incision 84.

Figure 26:
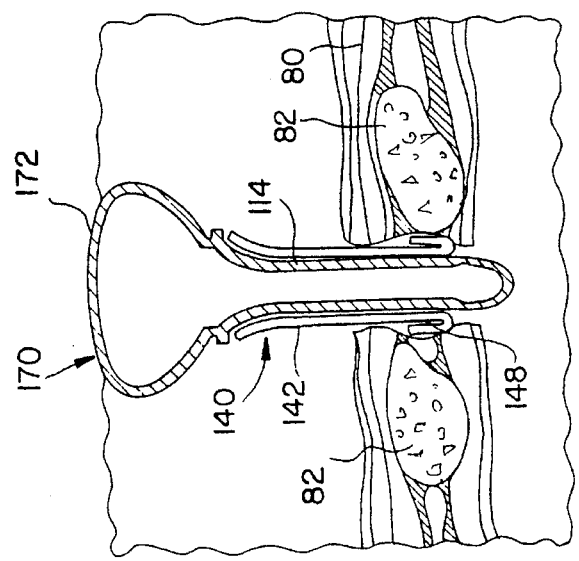
Figure 25:
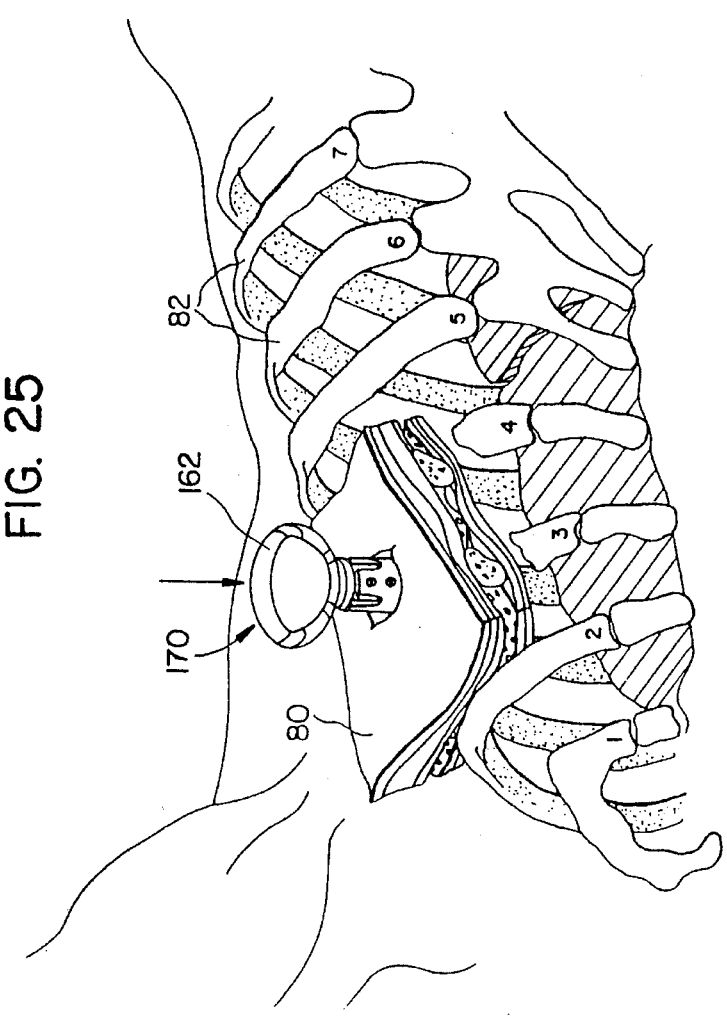

As shown in FIGS. 25 and 26, the trocar 170 is pushed into the incision 84 to insert the obturator 174 and the trocar tube or cannula 140 into the body wall. As the trocar 170 is advanced, the flange 148 is flexed upwardly by the body wall 80 to allow the tubular body 142 to pass through the body wall 80 between the adjacent ribs 82.

Figure 28:
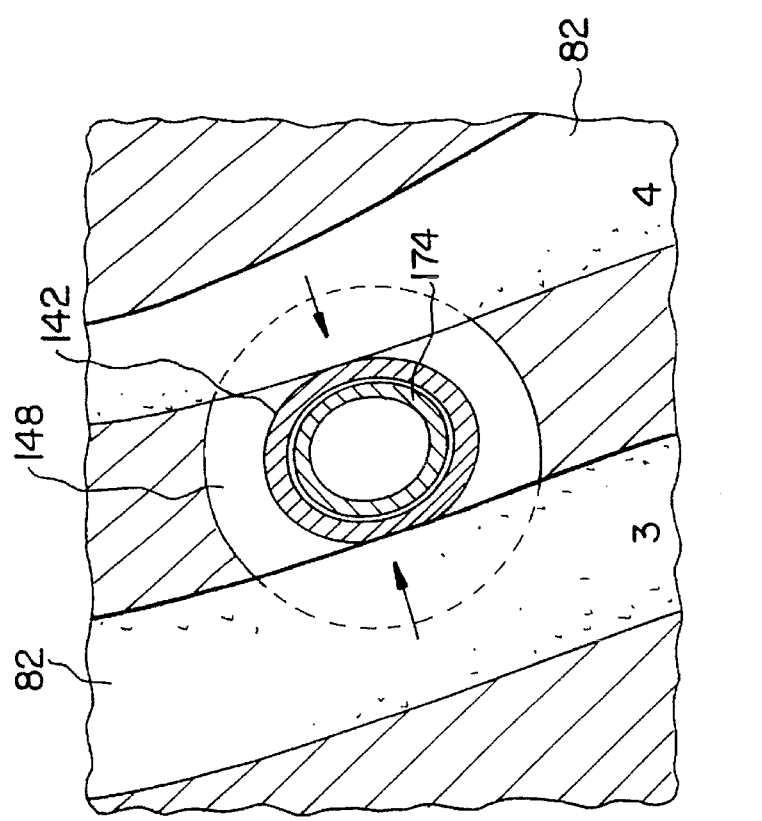
Figure 27:
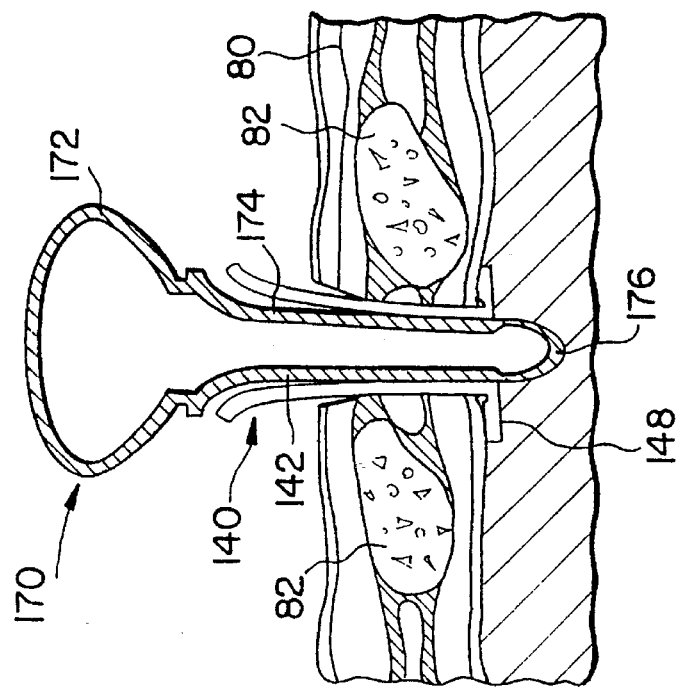

As shown in FIGS. 27 and 28, when the trocar tube or cannula 140 is fully inserted into the body wall 80, the flexible flange 148 returns to its natural position projecting radially outward from the tubular body 142 and the flange 148 engages the internal surface of the body wall 80.

Figure 30:
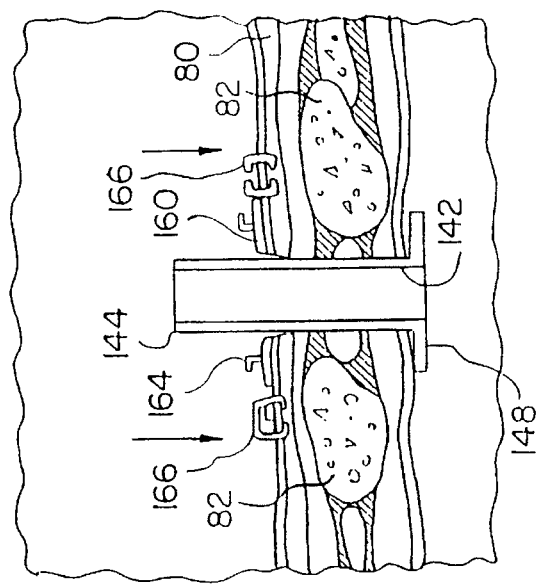
Figure 29:
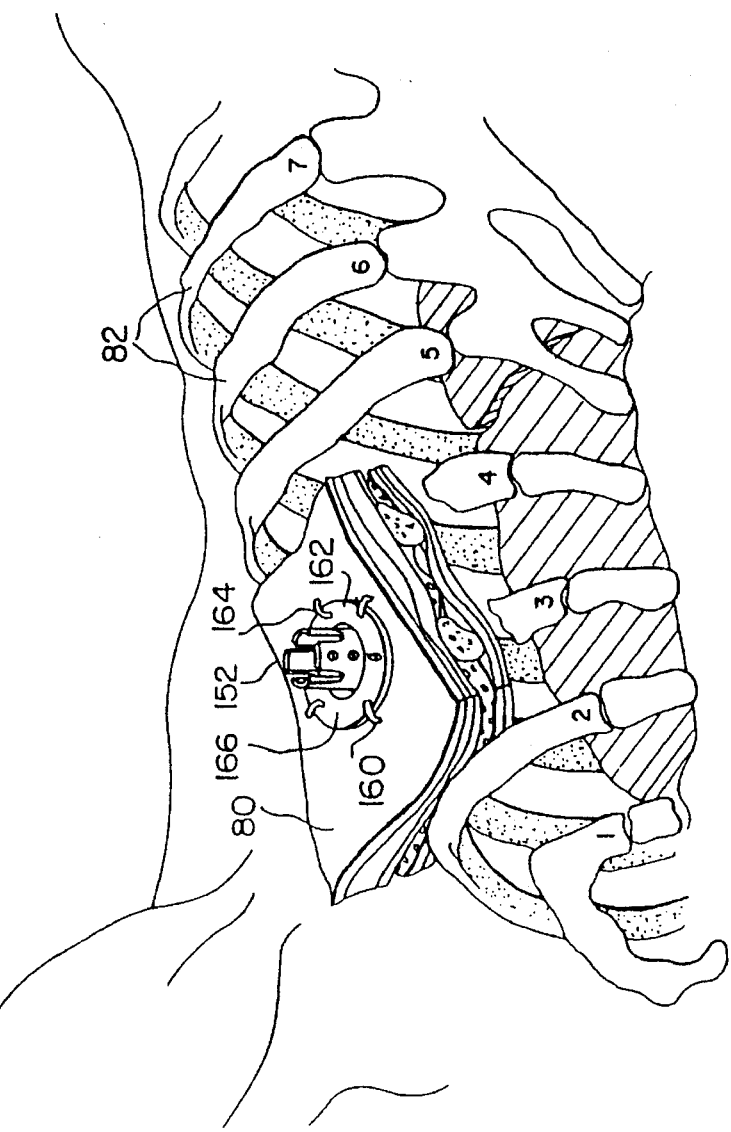

Referring to FIGS. 29 and 30, after the trocar tube or cannula 140 is fully inserted into the body wall 80, the trocar 170 is removed. The ring 160 is slipped over the outer or proximal end 144 of the tubular body 142 and the ring 160 is secured by staples 166 to the external surface of the body wall 80. The longitudinal score lines 150 are cut down to the vicinity of the ring 160 to divide the outer or proximal end 144 of the tubular body 142 into the flaps 152.

Figure 31:
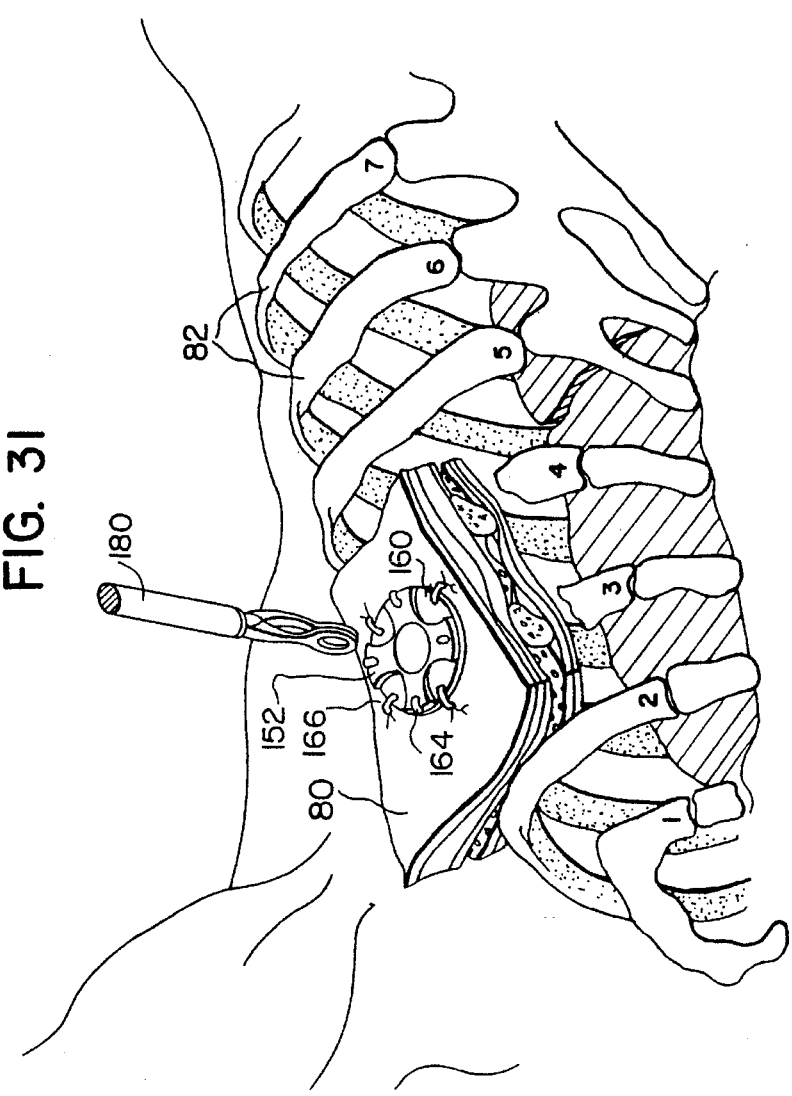
Figure 32:
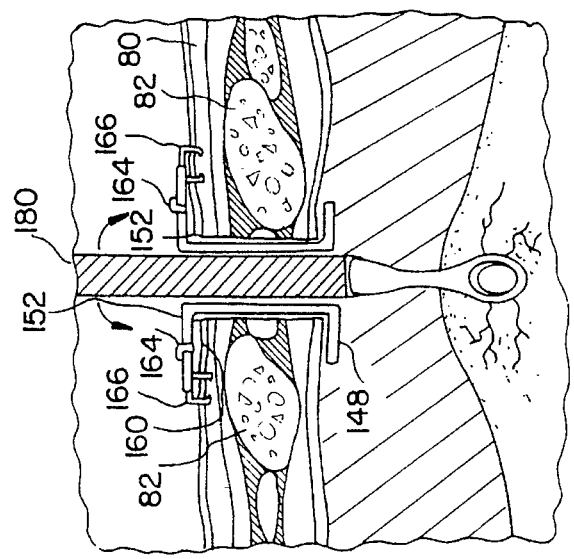
FIG. 32 shows the insertion of an endoscopic surgical tool into the trocar tube or cannula.

Referring to FIGS. 31 and 32, the flaps 152 are bent radially outward and downward into contact with the ring 160. The hook-like protrusions 164 on the ring 160 are punched through the partially formed holes or weakened areas 154 in the flaps 152 to secure the flaps 152 to the ring 160. Each flap 152 is stretched to the desired tension and pressed against the ring 152 to punch the hook-like protrusion 164 through the corresponding partially formed hole or weakened area 154 to secure the trocar tube or cannula 140 in the opening in the body wall 80. The annular flange 148 is firmly held against the internal surface of the body wall 80. The trocar tube or cannula 140 and the retainer ring 160 provide a surgical port in the body wall 80 through which endoscopic surgical instruments, e.g., a grasping forceps 180, can be inserted and manipulated inside the thoracic cavity.

Figure 33:
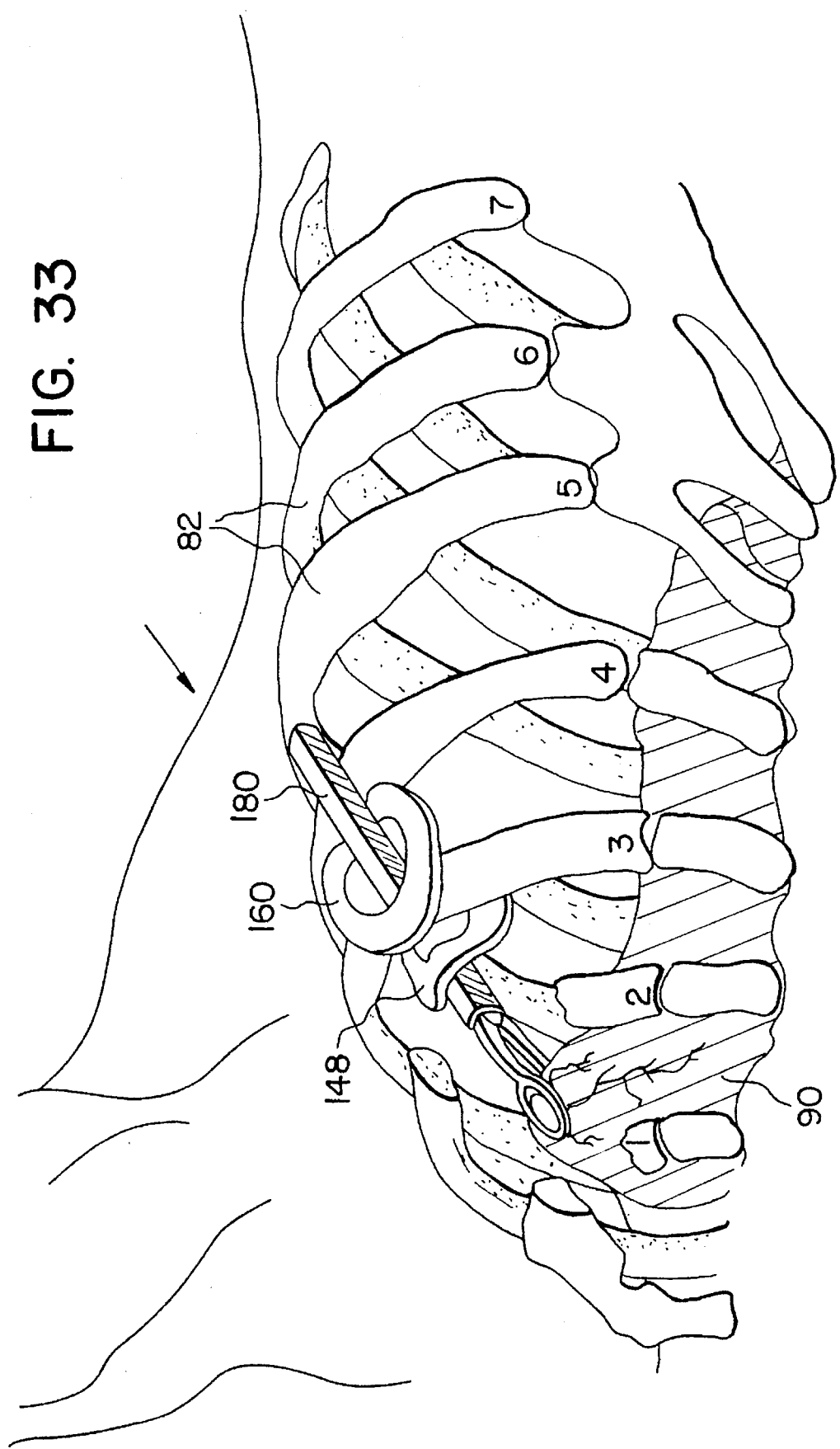
FIGS. 33 and 34 show the flexing of the trocar tube or cannula when the surgical tool is manipulated from side to side.
Figure 34:
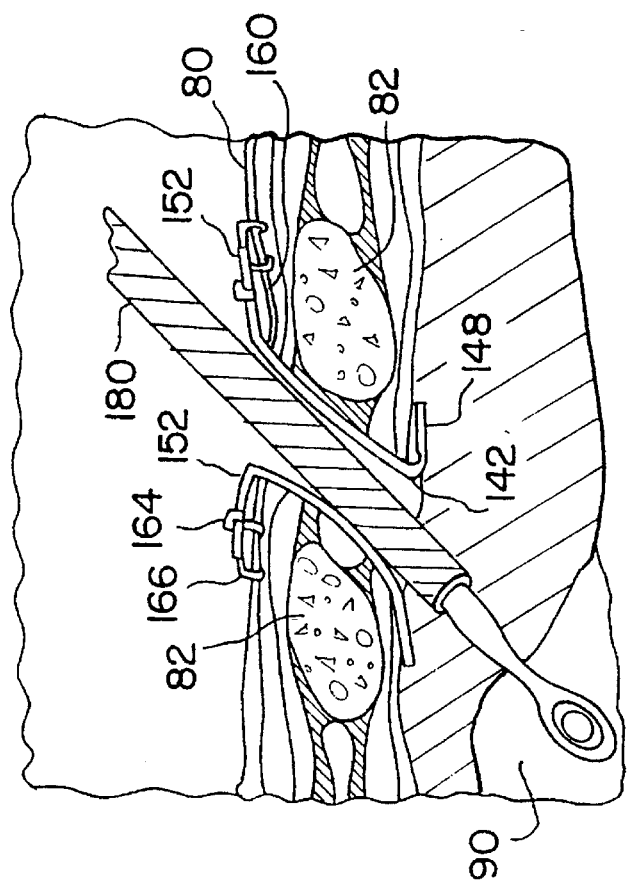

Referring to FIGS. 33 and 34, the flexibility of the trocar tube or cannula 140 allows a relatively severe angle of entry for the endoscopic instruments into the thoracic cavity. For example, the grasping forceps 180 can be inserted through the surgical port at a severe angle between the adjacent ribs 82 to allow the forceps to manipulate a collapsed lung 90. As shown in FIG. 34, the tubular body 142, the annular flange 148 and the flaps 152 are all capable of being flexed to permit the forceps 180 to be manipulated at different angles within the thoracic cavity. Also, the retainer ring 160 can be partially or completely made of flexible material to allow the forceps 180 to be moved from side to side at different angles with minimal interference from the surgical port. The flexibility of the trocar tube or cannula 140 permits severe angles of entry for the endoscopic instruments while maintaining an external surface flush with the body wall to avoid clutter in the exterior work space. Also, the flexible material of the trocar tube or cannula 140 acts as a cushion to protect the intercostal nerves and vessels, particularly at severe angles of entry by the endoscopic instruments.

Figure 35:
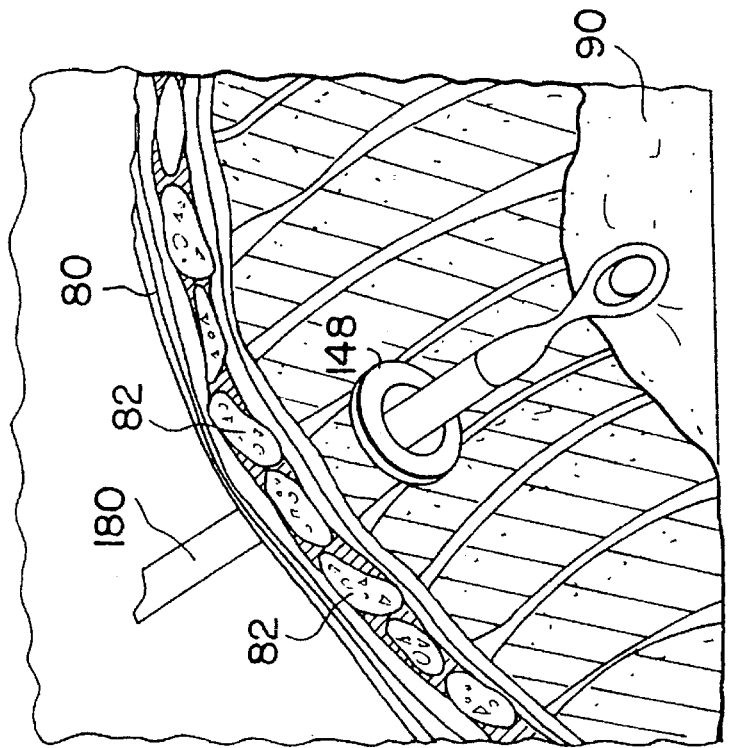
FIG. 35 is an interior perspective view of the trocar tube or cannula with the surgical tool inserted therein.

As shown in FIG. 35, the annular flange 148 is held against the internal surface of the body wall and presents a clean, smooth internal profile to allow maximum visualization and motion of the surgical instruments. Because the annular flange 148 and the retainer ring 160 are firmly held against the internal and external surfaces of the body wall 80, the surgical port provides enhanced tissue protection over the open incision in the body wall 80.

Figure 36:
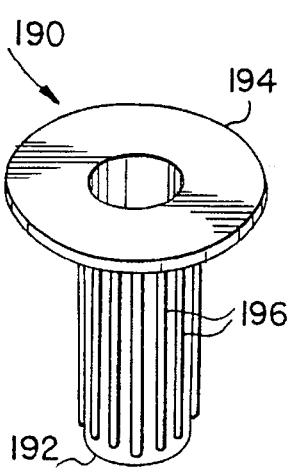
FIG. 36 is a perspective view of another embodiment of the trocar tube or cannula including longitudinal reinforcing ribs.
Figure 37:
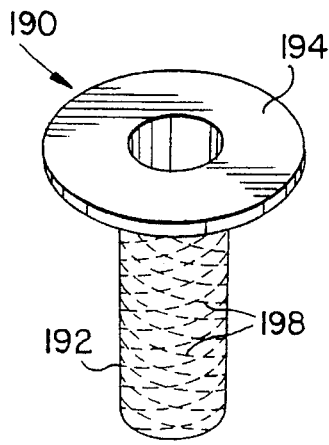
FIG. 37 is a perspective view of another embodiment of the trocar tube or cannula including criss-crossed reinforcing fibers.

In the embodiment of FIG. 36, a trocar tube or cannula 190 including a tubular body 192 and an annular flange 194 of flexible material is provided with a plurality of longitudinal reinforcing ribs 196 on the tubular body 192. The reinforcing ribs 196 enhance the axial stiffness of the tubular body 192 and permit bending of the tubular body 192 when endoscopic instruments are inserted into the trocar tube or cannula 190 and manipulated inside the body cavity. Alternatively, as shown in FIG. 37, the tubular body 192 may be provided with a plurality of criss-crossed reinforcing fibers 198 which enhance the axial stiffness and permit bending of the trocar tube or cannula 190.

Figure 38:
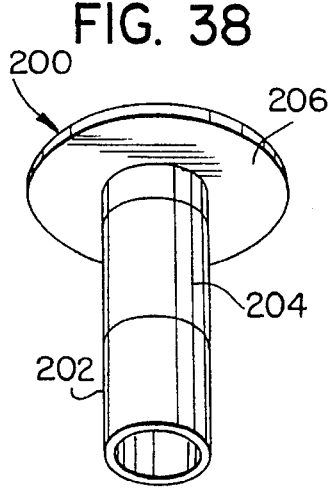
FIG. 38 is a perspective view of another embodiment of the trocar tube or cannula including an intermediate flexible tubular section.
Figure 39:
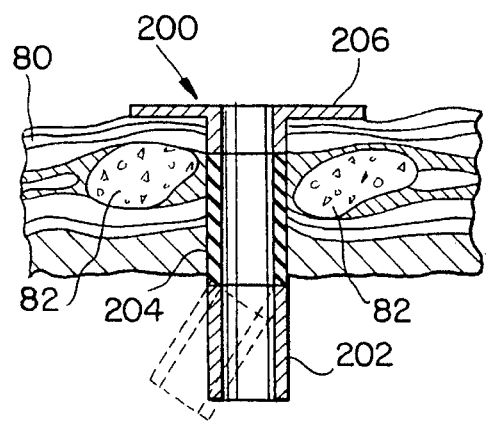

In the embodiment of FIGS. 38 and 39, a trocar tube or cannula 200 comprises a tubular body 202 of rigid material connected by a flexible tubular section 204 to an annular flange 206 of rigid material. When the trocar tube or cannula 200 is installed at an intercostal space in the body wall 80, the flexible tubular section 204 permits the rigid tubular body 202 to be deflected from side to side by an endoscopic instrument inserted through the trocar tube or cannula 200.

Figure 40:
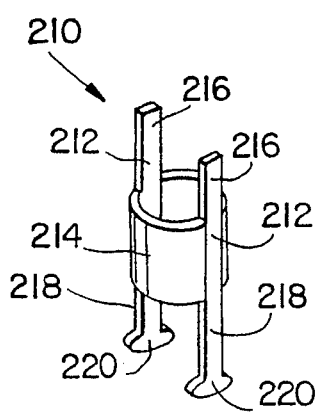
FIG. 40 is a perspective view of another embodiment of a trocar tube or cannula comprising a pair of stay rods of memory alloy connected by a flexible band.
Figure 41:
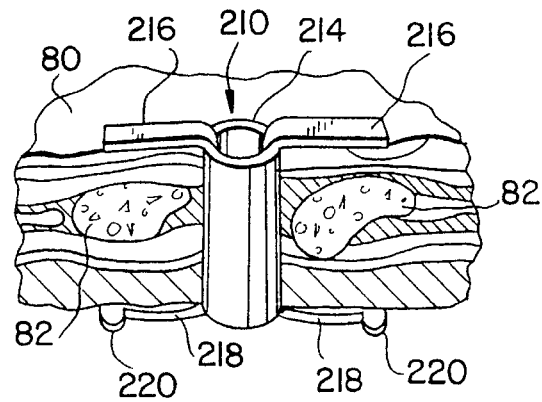

In the embodiment of FIGS. 40 and 41, a flexible thoracic port 210 comprises a pair of spaced, parallel stay rods 212 which are connected at the mid-sections by a flexible band 214. Each stay rod 212 consists of an elongated strip which has a curved or rounded cross section with its convex side oriented outward. Each stay rod 212 has outer or proximal end 216 extending above the flexible band 214 and an inner or distal end 218 extending below the flexible band 214. To facilitate installation, the proximal end 216 is slightly longer than the distal end 218 of each stay rod 212.

As shown in FIG. 40, the flexible band 214 consists of two thin strips of resilient material, e.g., polyurethane, connected to the mid-sections of the stay rods 212. Alternatively, the flexible band 214 consists of a single flexible strip which surrounds both stay rods 212. At the distal end of each stay rod 212 is a pair of flat, laterally extending flanges 220 which project outwardly from opposite edges of the stay rod 212.

The stay rods 212 consist of a material which allows the outer ends 214 and the inner ends 216 to bend in opposed radial directions extending outward from the flexible band 214. For example, the stay rods 212 can be made of a malleable metal which can be manually formed by digital manipulation into the configuration shown in FIG. 41 after the surgical port 210 is inserted into the opening in the body wall 80. Alternatively, each stay rod 212 can be made of a resilient material, e.g., stainless steel, with the legs 216 and 218 of the stay rods 212 preformed at right angles. To install the surgical port 210, the legs 214 and 216 are temporarily straightened as the surgical port 210 is inserted through a rigid trocar sleeve extending into the opening in the body wall 80. Thereafter, when the rigid trocar sleeve is removed, the stay rods 212 are released and the legs 216 and 218 spring back into the bent configuration shown in FIG. 41 curved around the ribs 82 in the body wall 80.

In an alternative embodiment, each stay rod 212 is made of a memory alloy, e.g., nitanol, which enables the stay rods 212 to assume the bent configuration shown in FIG. 41 when activated by a temperature change. Prior to installation, the stay rods 212 are straight, as shown in FIG. 40, to facilitate the insertion of the surgical port 210 into the opening in the body wall 80.

After the insertion of the flexible thoracic port 210 into the opening in the body wall 80, the memory alloy of the stay rods 212 is temperature activated, e.g., by the application of body heat, and the stay rods 212 assume the bent configuration shown in FIG. 41. The proximal or outer ends 216 of the stay rods 212 are bent laterally outward at right angles in opposite directions into contact with the external surface of the body wall 80. The distal or inner ends 218 of the stay rods 212 are bent laterally outward at right angles in opposite directions into contact with the internal surface of the body wall 80. The stay rods 212 curve over the ribs 82 and protect the nerves and vessels during the introduction, removal and manipulation of surgical instruments. The flexible band 214 permits the bent stay rods 212 to shift relative to each other as the surgical instruments are manipulated at different angles in the thoracic cavity. The flanges 220 tend to assume a flat configuration inside the thoracic cavity to protect the body wall 80 from trauma when a surgical instrument is inserted and manipulated within the surgical port 210.

The flexible surgical port 210 with nitanol stay rods 212 can be introduced into an opening at an intercostal space in the body wall 80 by using a conventional rigid trocar as follows. A rigid trocar tube and obturator are inserted through an incision into the intercostal space in the body wall 80. The obturator is removed leaving the rigid trocar tube inserted in the intercostal space. Then the flexible surgical port 210 is inserted through the rigid trocar tube with the flanges 220 extending into the thoracic cavity. The memory alloy of the stay rods 212 is activated by applying heat while sliding the flexible surgical port 210 along the rigid trocar tube into the intercostal space. The rigid trocar tube is removed to allow the memory alloy of the stay rods 212 to assume the bent configuration shown in FIG. 41 curved around the ribs 82 in the body wall 80.

Alternatively, the flexible surgical port 210 can be inserted into the intercostal space in the body wall 80 by using a double lumen trocar including an inner trocar sleeve of smaller diameter housed within an outer trocar sleeve of larger diameter. The flexible surgical port 210 is inserted into the space between the two sleeves of the trocar. After insertion of the trocar into the intercostal space, the obturator is removed and heat is applied to the trocar sleeves to actuate the memory alloy of the stay rods 212. Then the trocar sleeves are removed from the intercostal space to allow the memory alloy of the stay rods 212 to assume the bent configuration shown in FIG. 41 curved around the ribs 82 in the body wall 80. Similarly, the double lumen trocar can be used to install the flexible surgical port 210 with preformed stay rods 212.

Referring to FIG. 42, a surgical instrument or obturator, generally 250, is provided to facilitate the installation of a flexible trocar tube or cannula of relatively large diameter at an intercostal space in the body wall. The obturator 250 comprises a pair of elongated handles 252 and 254 pivotally connected by a pivot pin 256 in a reverse pliers arrangement. A pair of sleeve-like finger grips 258 and 260 cover the rear portions of handles 252 and 254, respectively, to facilitate the handling and operation of the obturator 250 by a surgeon. The handles 252 and 254 have front arms 262 and 264, respectively, which are connected by pivot pins 266 and 268 (FIG. 43) to a pair of obturator jaws 270 and 272, respectively. A coil spring 274 is provided with spring arms 276 and 278 connected to the handles 252 and 254 rearwardly of the pivot pin 256 to normally bias the handles 252 and 254 apart and urge the front arms 262 and 264 together to maintain the obturator jaws 270 and 272 in the closed position (FIG. 43).

The obturator jaw 270 consists of an elongated metal bar, preferably made of stainless steel, which is generally rectangular in configuration and includes an enlarged rectangular support block 274 at its proximal end connected by the pivot pin 266 to the front arm 262 of the handle 252. Similarly, the obturator jaw 272 comprises an elongated metal bar, preferably made of stainless steel, which is generally rectangular in configuration and includes an enlarged rectangular support block 276 at its proximal end connected by the pivot pin 268 to the front arm 264 of the handle 254. The support blocks 274 and 276 have front vertical edges 275 and 277 offset from the obturator jaws 272 and 274, respectively, for engaging the proximal end of the trocar tube or cannula 120 (FIG. 45).

A guide pin 278 is fixed, e.g., by welding, in a vertical bore 280 in the lower obturator jaw 272 and is slidably received in a vertical bore 282 formed in the upper obturator jaw 270. The guide pin 278 maintains the obturator jaws 270 and 272 in parallel alignment when the front arms 262 and 264 are moved apart by squeezing the handles 252 and 254 together. A stop pin 284 with enlarged heads 286 and 288 at its opposite ends is slidably received in vertical bores 290 and 292 formed in the obturator jaws 270 and 272, respectively. The stop pin 284 limits the amount of separation of the obturator jaws 270 and 272 when the handles 252 and 254 are squeezed together.

As shown in FIG. 46, the obturator jaws 270 and 272 have flat elongated opposing surfaces 294 and 296 which are moved into engagement when the obturator jaws 270 and 272 are closed. Also, as shown in FIG. 50, the obturator jaws 270 and 272 have elongated semi-cylindrical exterior surfaces 298 and 300, respectively, for engaging the tubular body 122 of the trocar tube or cannula 120 when the obturator jaws 270 and 272 are inserted therein.

Referring to FIG. 42, a pair of conically tapered pointed tips 302 and 304 is mounted at the distal ends of the obturator jaws 270 and 272, respectively. The upper conical tip 302 supports a knife blade 306 which is exposed when the obturator jaws 270 and 272 are separated to cut the tissue at an intercostal location as the obturator jaws 270 and 272 are inserted into the body wall.

As shown in FIGS. 45–47, the upper conical tip 302 has a narrow vertical slot 308 extending therethrough for receiving the knife blade 306 which is secured to the conical tip 302 by a cross pin 310. The lower conical tip 304 has a narrow vertical slot 312 for slidably receiving the knife blade 306. A pair of mounting posts 314 and 316 at the proximal ends of the conical tips 302 and 304 is received in a pair of axial openings at the distal ends of the obturator jaws 270 and 272, respectively. The mounting posts 314 and 316 are secured to the obturator jaws 270 and 272 by set screws 318 and 320, respectively. The conical tips 302 and 304 have rear vertical edges 322 and 324 which are offset from the obturator jaws 272 and 274, respectively, for engaging the distal end of the trocar tube or cannula 120 (FIG. 45).

The following procedure is performed by using the obturator 250 (FIG. 42) to install the trocar tube or cannula 120 (FIG. 10) at an intercostal location in the body wall. The obturator jaws 270 and 272 in the closed position (FIG. 45) are inserted into the flanged end of the tubular trocar body 122. The trocar tube or cannula 120 is positioned on the obturator jaws 270 and 272 with the flange 128 engaging the front edges 275 and 277 of the support blocks 274 and 276, respectively. The distal end of the trocar tube or cannula is located adjacent to the rear edges 322 and 324 on the pointed tips 302 and 304. With the obturator jaws 270 and 272 closed, the tubular trocar body 122 remains in its natural circular cross section (FIG. 50).

By squeezing the handles 252 and 254 together, the obturator jaws 270 and 272 are opened (FIG. 46) to stretch the tubular trocar body 122 into an ovoid shape (FIG. 51). Then the obturator jaws 270 and 272 are aligned with and pushed into an incision at an intercostal location to insert the trocar tube or cannula into the body wall. The ovoid shape of the trocar body 122 facilitates the insertion of the trocar tube or cannula 120 between the adjacent ribs at the intercostal location. The knife blade 306 cuts through the tissue of the body wall as the obturator jaws 270 and 272 are pushed into the incision. The trocar tube or cannula 120 is advanced into the body wall by the obturator jaws 270 and 272 until the flange 128 engages the external surface of the body wall. Then the obturator jaws 270 and 272 are closed by relaxing the squeezing forces applied to the handles 252 and 254. The obturator jaws 270 and 272 are returned to the closed position by the coil spring 274 which biases the handles 252 and 254 apart. Then, by pulling on the handles 252 and 254, the closed obturator jaws 270 and 272 are removed from the trocar tube or cannula 120. Thereafter, the flange 128 is secured to the external surface of the body by staples, sutures, adhesives or other suitable fasteners.

The invention in its broader aspects is not limited to the specific details of the preferred embodiments shown and described, and those skilled in the art will recognize that the invention can be practiced with modification within the spirit and scope of the appended claims.

We claim:

1. A trocar assembly for inserting a flexible trocar tube into an opening at an intercostal location in a body wall, comprising:

an elongated trocar obturator having a collar spaced proximally from the distal end of said obturator;

an elongated trocar tube of flexible material comprising a hollow tubular body having a substantially circular cross section with an annular flange projecting radially outward from one end of said tubular body; and said trocar obturator being insertable into said hollow tubular body of said trocar tube with said collar engaging said flange and said distal end extending from said hollow tubular body for inserting said trocar tube into the opening at the intercostal location in the body wall; and wherein said obturator has an oval-shaped cross section adapted to stretch the flexible trocar tube into an ovoid shape sufficiently narrow in width to fit between the ribs at the intercostal location in the body wall.

2. The trocar assembly of claim 1, wherein:

said collar is slidably mounted on said trocar obturator and adapted to remain in engagement with said flange as said trocar obturator is withdrawn from said trocar tube.

* * * * *